(12) United States Patent
Yellin

(10) Patent No.: US 11,617,647 B2
(45) Date of Patent: Apr. 4, 2023

(54) TRANSCATHETER PROSTHETIC VALVE FOR MITRAL OR TRICUSPID VALVE REPLACEMENT

(71) Applicant: VALCARE, INC., Wilmington, DE (US)

(72) Inventor: Nadav Yellin, Even Yehuda (IL)

(73) Assignee: VALCARE, INC., Herzelyia Pituach (IL)

( * ) Notice: Subject to any disclaimer, the term of this patent is extended or adjusted under 35 U.S.C. 154(b) by 345 days.

(21) Appl. No.: 17/080,592

(22) Filed: Oct. 26, 2020

(65) Prior Publication Data

US 2021/0038381 A1 Feb. 11, 2021

Related U.S. Application Data

(62) Division of application No. 15/584,110, filed on May 2, 2017, now Pat. No. 10,813,751, which is a division
(Continued)

(51) Int. Cl.
*A61F 2/24* (2006.01)

(52) U.S. Cl.
CPC .......... *A61F 2/2418* (2013.01); *A61F 2/2409* (2013.01); *A61F 2/2427* (2013.01);
(Continued)

(58) Field of Classification Search
CPC ............ A61F 2/24–2424; A61F 2/2475; A61F 2230/0067; A61F 2250/0039; A61F 2220/0008; A61F 2250/0069
See application file for complete search history.

(56) References Cited

U.S. PATENT DOCUMENTS

| 4,602,911 A | 7/1986 | Ahmadi et al. |
| 5,236,440 A | 8/1993 | Hlavacek et al. |

(Continued)

FOREIGN PATENT DOCUMENTS

| DE | 102014102653 A1 | 9/2015 |
| EP | 2600799 | 6/2013 |

(Continued)

OTHER PUBLICATIONS 12793292.9, et al., Extended European Search Report, dated Dec. 1, 2014, 6 pages.

(Continued)

*Primary Examiner* — Rebecca S Preston
(74) *Attorney, Agent, or Firm* — Dorsey & Whitney LLP

(57) ABSTRACT

A prosthesis secures a replacement valve in a heart. The prosthesis includes a radially expandable inflow section and outflow section, and migration blocker rods. The inflow section has a tapered shape and is implanted within an atrium of a heart adjacent a native valve annulus. The outflow section couples to the inflow section, and is configured to be implanted through the native valve annulus and at least partially within a ventricle of the heart. The migration blocker rods extend circumferentially around at least a portion of the outflow section and hold native leaflets of the heart valve. In a contracted configuration, the prosthesis may be implanted through a catheter into the heart. In an expanded configuration, the tapered shape of the inflow section in the atrium cooperates with the migration blockers in the ventricle to hold the prosthesis against the native valve annulus.

17 Claims, 31 Drawing Sheets

Related U.S. Application Data of application No. 14/891,189, filed as application No. PCT/US2013/042275 on May 22, 2013, now abandoned.

(52) U.S. Cl.
CPC . *A61F 2210/0014* (2013.01); *A61F 2220/005* (2013.01); *A61F 2220/0008* (2013.01); *A61F 2220/0016* (2013.01); *A61F 2220/0033* (2013.01); *A61F 2220/0058* (2013.01); *A61F 2220/0075* (2013.01); *A61F 2230/0006* (2013.01); *A61F 2230/0008* (2013.01); *A61F 2230/0054* (2013.01); *A61F 2230/0067* (2013.01); *A61F 2250/006* (2013.01); *A61F 2250/0039* (2013.01); *A61F 2250/0048* (2013.01); *A61F 2250/0069* (2013.01)

(56) References Cited

U.S. PATENT DOCUMENTS

| | | |
|---|---|---|
| 5,306,296 A | 4/1994 | Wright et al. |
| 5,695,518 A | 12/1997 | Laerum |
| 5,716,370 A | 2/1998 | Williamson, IV et al. |
| 5,855,614 A | 1/1999 | Stevens et al. |
| 6,113,611 A | 9/2000 | Allen et al. |
| 6,231,602 B1 | 5/2001 | Carpentier et al. |
| 6,619,291 B2 | 9/2003 | Hlavka et al. |
| 6,629,534 B1 | 10/2003 | St. Goar et al. |
| 6,689,048 B2 | 2/2004 | Vanden Hoek et al. |
| 6,726,704 B1 | 4/2004 | Loshakove et al. |
| 6,776,784 B2 | 8/2004 | Ginn |
| 6,790,229 B1 | 9/2004 | Berreklouw |
| 6,797,002 B2 | 9/2004 | Spence et al. |
| 6,805,711 B2 | 10/2004 | Quijano et al. |
| 6,893,459 B1 | 5/2005 | Macoviak |
| 7,101,395 B2 | 9/2006 | Tremulis et al. |
| 7,114,953 B1 | 10/2006 | Wagner |
| 7,175,660 B2 | 2/2007 | Cartledge et al. |
| 7,238,191 B2 | 7/2007 | Bachmann |
| 7,285,087 B2 | 10/2007 | Moaddeb et al. |
| 7,297,150 B2 | 11/2007 | Cartledge et al. |
| 7,569,072 B2 | 8/2009 | Berg et al. |
| 7,594,887 B2 | 9/2009 | Moaddeb et al. |
| 7,635,329 B2 | 12/2009 | Goldfarb et al. |
| 7,655,040 B2 | 2/2010 | Douk et al. |
| 7,717,954 B2 | 5/2010 | Solem et al. |
| 7,722,668 B2 | 5/2010 | Moaddeb et al. |
| 7,758,637 B2 | 7/2010 | Starksen et al. |
| 7,837,729 B2 | 11/2010 | Gordon et al. |
| 7,988,725 B2 | 8/2011 | Gross et al. |
| 8,163,014 B2 | 4/2012 | Lane et al. |
| 8,182,529 B2 | 5/2012 | Gordon et al. |
| 8,236,049 B2 | 8/2012 | Rowe et al. |
| 8,287,591 B2 | 10/2012 | Keidar et al. |
| 8,518,107 B2 | 8/2013 | Tsukashima et al. |
| 8,579,968 B1 | 11/2013 | Shannon et al. |
| 2002/0151961 A1 | 10/2002 | Lashinski et al. |
| 2002/0151970 A1 | 10/2002 | Garrison et al. |
| 2002/0188170 A1 | 12/2002 | Santamore et al. |
| 2002/0198526 A1 | 12/2002 | Shaolian et al. |
| 2003/0050693 A1 | 3/2003 | Quijano et al. |
| 2003/0078465 A1 | 4/2003 | Pai |
| 2003/0078671 A1 | 4/2003 | Lesniak et al. |
| 2003/0191528 A1 | 10/2003 | Quijano et al. |
| 2003/0198605 A1 | 10/2003 | Montgomery et al. |
| 2003/0199974 A1 | 10/2003 | Lee et al. |
| 2004/0044364 A1 | 3/2004 | Devries et al. |
| 2004/0068276 A1 | 4/2004 | Golden et al. |
| 2004/0122514 A1 | 6/2004 | Fogarty et al. |
| 2004/0138744 A1 | 7/2004 | Lashinski et al. |
| 2004/0148021 A1 | 7/2004 | Cartledge et al. |
| 2004/0193191 A1 | 9/2004 | Starksen et al. |
| 2004/0243230 A1 | 12/2004 | Navia et al. |
| 2004/0249391 A1 | 12/2004 | Cummins |
| 2004/0260393 A1 | 12/2004 | Rahdert et al. |
| 2004/0260394 A1 | 12/2004 | Douk et al. |
| 2005/0020696 A1 | 1/2005 | Montgomery et al. |
| 2005/0033325 A1 | 2/2005 | May et al. |
| 2005/0065550 A1 | 3/2005 | Starksen et al. |
| 2005/0090846 A1 | 4/2005 | Pedersen et al. |
| 2005/0096740 A1 | 5/2005 | Langberg et al. |
| 2005/0113910 A1 | 5/2005 | Paniagua et al. |
| 2005/0137695 A1 | 6/2005 | Salahieh et al. |
| 2005/0203549 A1 | 9/2005 | Realyvasquez |
| 2005/0222678 A1 | 10/2005 | Lashinski et al. |
| 2005/0240200 A1 | 10/2005 | Berghaim |
| 2005/0267572 A1 | 12/2005 | Schoon et al. |
| 2005/0283190 A1 | 12/2005 | Huitema et al. |
| 2005/0288778 A1 | 12/2005 | Shaoulian et al. |
| 2005/0288781 A1 | 12/2005 | Moaddeb et al. |
| 2006/0009737 A1 | 1/2006 | Whiting et al. |
| 2006/0129025 A1 | 6/2006 | Levine et al. |
| 2006/0155165 A1 | 7/2006 | Vanden Hoek et al. |
| 2006/0161169 A1 | 7/2006 | Nieminen et al. |
| 2006/0184240 A1 | 8/2006 | Jimenez et al. |
| 2006/0184242 A1 | 8/2006 | Lichtenstein |
| 2006/0195134 A1 | 8/2006 | Crittenden et al. |
| 2006/0195183 A1 | 8/2006 | Navia et al. |
| 2006/0241748 A1 | 10/2006 | Lee et al. |
| 2006/0282161 A1 | 12/2006 | Huynh et al. |
| 2007/0016287 A1 | 1/2007 | Cartledge et al. |
| 2007/0027533 A1 | 2/2007 | Douk et al. |
| 2007/0038296 A1 | 2/2007 | Navia et al. |
| 2007/0051377 A1 | 3/2007 | Douk et al. |
| 2007/0067027 A1 | 3/2007 | Maddeb et al. |
| 2007/0073098 A1 | 3/2007 | Lenker et al. |
| 2007/0080188 A1 | 4/2007 | Spence et al. |
| 2007/0093854 A1 | 4/2007 | Kayan |
| 2007/0118215 A1 | 5/2007 | Moaddeb |
| 2007/0128132 A1 | 6/2007 | Piergallini et al. |
| 2007/0135913 A1 | 6/2007 | Moaddeb et al. |
| 2007/0142907 A1 | 6/2007 | Moaddeb et al. |
| 2007/0213812 A1 | 9/2007 | Webler et al. |
| 2007/0233239 A1 | 10/2007 | Navia et al. |
| 2007/0239272 A1 | 10/2007 | Navia et al. |
| 2007/0244553 A1 | 10/2007 | Rafiee et al. |
| 2007/0244554 A1 | 10/2007 | Rafiee et al. |
| 2007/0244555 A1 | 10/2007 | Rafiee et al. |
| 2007/0244556 A1 | 10/2007 | Rafiee et al. |
| 2007/0250161 A1 | 10/2007 | Dolan |
| 2007/0293942 A1 | 12/2007 | Mirzaee |
| 2008/0177380 A1 | 7/2008 | Starksen et al. |
| 2008/0177381 A1 | 7/2008 | Navia et al. |
| 2008/0243220 A1 | 10/2008 | Barker |
| 2008/0262513 A1 | 10/2008 | Stahler et al. |
| 2008/0262609 A1 | 10/2008 | Gross et al. |
| 2008/0306586 A1 | 12/2008 | Cartledge et al. |
| 2009/0088838 A1 | 4/2009 | Shaolian et al. |
| 2009/0118747 A1 | 5/2009 | Bettuchi et al. |
| 2009/0149872 A1 | 6/2009 | Gross et al. |
| 2009/0216322 A1 | 8/2009 | Le et al. |
| 2009/0222083 A1 | 9/2009 | Nguyen et al. |
| 2009/0238778 A1 | 9/2009 | Mordas et al. |
| 2009/0299470 A1 | 12/2009 | Rao et al. |
| 2010/0010616 A1 | 1/2010 | Drews et al. |
| 2010/0030014 A1 | 2/2010 | Ferrazzi et al. |
| 2010/0063586 A1 | 3/2010 | Hasenkam et al. |
| 2010/0121433 A1 | 5/2010 | Bolling et al. |
| 2010/0161047 A1 | 6/2010 | Cabiri |
| 2010/0185274 A1 | 7/2010 | Moaddeb et al. |
| 2010/0211166 A1 | 8/2010 | Miller et al. |
| 2010/0249920 A1 | 9/2010 | Bolling |
| 2010/0266989 A1 | 10/2010 | Piergallini et al. |
| 2010/0280605 A1 | 11/2010 | Hammer et al. |
| 2010/0286767 A1 | 11/2010 | Zipory et al. |
| 2011/0022168 A1 | 1/2011 | Cartledge |
| 2011/0027753 A1 | 2/2011 | Maurat et al. |
| 2011/0034953 A1 | 2/2011 | Milo |
| 2011/0066231 A1 | 3/2011 | Cartledge et al. |
| 2011/0093062 A1 | 4/2011 | Cartledge et al. |
| 2011/0106245 A1 | 5/2011 | Miller et al. |
| 2011/0106247 A1 | 5/2011 | Miller et al. |
| 2011/0137397 A1 | 6/2011 | Chau et al. |

(56) References Cited

U.S. PATENT DOCUMENTS

| | | |
|---|---|---|
| 2011/0166649 A1 | 7/2011 | Gross et al. |
| 2011/0190879 A1 | 8/2011 | Bobo et al. |
| 2011/0208298 A1 | 8/2011 | Tuval et al. |
| 2011/0224785 A1 | 9/2011 | Hacohen |
| 2011/0257728 A1 | 10/2011 | Kuehn |
| 2011/0282361 A1 | 11/2011 | Miller et al. |
| 2011/0301698 A1 | 12/2011 | Miller et al. |
| 2011/0301699 A1 | 12/2011 | Saadat et al. |
| 2012/0022557 A1 | 1/2012 | Cabiri et al. |
| 2012/0022644 A1 | 1/2012 | Reich et al. |
| 2012/0059458 A1 | 3/2012 | Buchbinder et al. |
| 2012/0095455 A1 | 4/2012 | Rodmond et al. |
| 2012/0123531 A1 | 5/2012 | Fsukashima et al. |
| 2012/0136436 A1 | 5/2012 | Cabiri et al. |
| 2012/0165930 A1 | 6/2012 | Hanson et al. |
| 2012/0245604 A1 | 9/2012 | Tegzes |
| 2012/0310330 A1 | 12/2012 | Buchbinder et al. |
| 2013/0087598 A1 | 4/2013 | Surti |
| 2013/0116780 A1 | 5/2013 | Miller et al. |
| 2013/0166022 A1 | 6/2013 | Conklin |
| 2013/0204361 A1 | 8/2013 | Adams et al. |
| 2013/0226289 A1 | 8/2013 | Shaolian et al. |
| 2013/0226290 A1 | 8/2013 | Yellin et al. |
| 2013/0282114 A1 | 10/2013 | Schweich, Jr. et al. |
| 2013/0289718 A1 | 10/2013 | Tsukashima et al. |
| 2013/0289720 A1 | 10/2013 | Dobrilovic |
| 2013/0304197 A1 | 11/2013 | Buchbiner et al. |
| 2014/0005778 A1 | 1/2014 | Buchbinder et al. |
| 2014/0046433 A1 | 2/2014 | Kovalsky |
| 2014/0058505 A1 | 2/2014 | Bielefeld |
| 2014/0114407 A1 | 4/2014 | Rajamannan |
| 2014/0214157 A1* | 7/2014 | Bortlein .................. A61F 2/243 623/2.11 |
| 2015/0173897 A1 | 6/2015 | Raanani et al. |
| 2015/0173987 A1 | 6/2015 | Albinmousa et al. |
| 2015/0351903 A1 | 12/2015 | Morriss et al. |
| 2016/0022419 A1 | 1/2016 | Yellin et al. |
| 2016/0038286 A1 | 2/2016 | Yellin et al. |
| 2016/0089235 A1 | 3/2016 | Yellin |
| 2016/0106420 A1 | 4/2016 | Foerster et al. |
| 2016/0120642 A1 | 5/2016 | Shaolian et al. |
| 2016/0120645 A1 | 5/2016 | Alon |
| 2017/0042670 A1 | 2/2017 | Shaolian et al. |
| 2017/0231763 A1 | 8/2017 | Yellin |
| 2018/0042723 A1 | 2/2018 | Yellin et al. |

FOREIGN PATENT DOCUMENTS

| | | |
|---|---|---|
| KR | 1020040095482 A | 11/2004 |
| RU | 125062 U1 | 2/2013 |
| WO | 199009153 A1 | 2/1990 |
| WO | 2003017874 A1 | 3/2003 |
| WO | 2003047467 A1 | 6/2003 |
| WO | 2005046488 A2 | 5/2005 |
| WO | 2009052427 A1 | 4/2009 |
| WO | 2009120764 A2 | 10/2009 |
| WO | 2010004546 A1 | 1/2010 |
| WO | 2010085659 A1 | 7/2010 |
| WO | 2011011443 A1 | 1/2011 |
| WO | 2011097355 A2 | 8/2011 |
| WO | 2012004679 A2 | 1/2012 |
| WO | 2012019052 A1 | 2/2012 |
| WO | 2012063228 A1 | 5/2012 |
| WO | 2012095159 A2 | 6/2012 |
| WO | 2012106354 A1 | 8/2012 |
| WO | 2012167095 A2 | 12/2012 |
| WO | 2013095816 A1 | 6/2013 |
| WO | 2013128436 A1 | 9/2013 |
| WO | 2013130641 A1 | 9/2013 |
| WO | 2013175468 A2 | 11/2013 |
| WO | 2014145399 A1 | 9/2014 |
| WO | 2014189509 A1 | 11/2014 |
| WO | 2014190329 A1 | 11/2014 |
| WO | 2014210600 A2 | 12/2014 |

OTHER PUBLICATIONS 13755441.6, et al., Partial European Search Report, dated Nov. 3, 2015 ,7 pages.
13885021.9, et al., Extended European Search Report, dated Jan. 3, 2017 ,8 pages.
14762806.9, et al., Extended European Search Report, dated Jul. 29, 2016 ,7 pages.
14801009.3, et al., Extended European Search Report, dated Dec. 5, 2016 ,8 pages.
17155803.4, et al., Extended European Search Report, dated Aug. 9, 2017 ,7 pages.
PCT/US2019/064289, et al., International Search Report and Written Opinion, dated Feb. 5, 2020.
Lendlein, et al., Biodegradable, Elastic Shape-Memory Polymers for Potential Biomedical Applications, Science, vol. 296 ,May 31, 2002 ,pp. 1673-1676.
PCT/US2011/046659, et al., International Search Report and Written Opinion , dated Jun. 4, 2012 ,13 pages.
PCT/US2012/040481, et al., International Search Report and Written Opinion, dated Dec. 6, 2012 ,12 pages.
PCT/US2013/028065, et al., International Search Report and Written Opinion, dated Jun. 27, 2013 ,12 pages.
PCT/US2013/042275, et al., International Search Report and Written Opinion, dated Feb. 20, 2014 ,18 pages.
PCT/US2013/058102, et al., International Search Report and Written Opinion, dated Apr. 21, 2014.
PCT/US2013/073552, et al., International Search Report and Written Opinion, dated Mar. 6, 2014 ,4 pages.
PCT/US2014/030163, et al., International Search Report and Written Opinion, dated Aug. 27, 2014 ,12 pages.
PCT/US2014/039545, et al., International Search Report and Written Opinion, dated Oct. 22, 2014.
PCT/US2014/044920, et al., International Search Report and Written Opinion, dated Dec. 24, 2014 ,14 pages.
PCT/US2017/046933, et al., International Search Report and Written Opinion, dated Dec. 21, 2017 ,10 pages.
PCT/US2018/022910, et al., International Search Report and Written Opinion, dated May 23, 2018 ,6 pages.
19170261.2, et al., Extended European Search Report, dated Aug. 5, 2019 ,9 pages.

* cited by examiner

TRANSCATHETER PROSTHETIC VALVE FOR MITRAL OR TRICUSPID VALVE REPLACEMENT

CROSS-REFERENCE TO RELATED APPLICATION

The present application is a divisional application of U.S. patent application Ser. No. 15/584,110 entitled, "TRANSCATHETER PROSTHETIC VALVE FOR MITRAL OR TRICUSPID VALVE REPLACEMENT," filed on May 2, 2017, which is a divisional application of U.S. patent application Ser. No. 14/891,189 entitled, "TRANSCATHETER PROSTHETIC VALVE FOR MITRAL OR TRICUSPID VALVE REPLACEMENT," filed on Nov. 13, 2015, which is a U.S. national stage filing under 35 U.S.C. § 371 of International Application No. PCT/US2013/042275 filed on May 22, 2013 entitled "TRANSCATHETER PROSTHETIC VALVE FOR MITRAL OR TRICUSPID VALVE REPLACEMENT," each of which is incorporated herein by reference in its entirety.

TECHNICAL FIELD

The present disclosure relates to implantable prosthetic devices. The disclosure is particularly useful in prosthetic devices implantable by catheter for the treatment of mitral or tricuspid regurgitation. The cause of the regurgitation can be either functional or degenerative or any other reason. Certain disclosed embodiments may be used for other valvular lesions as well.

BACKGROUND

Mitral Regurgitation is a valvular dysfunction that causes blood volume to flow during systolic (during left ventricular contraction) from the left ventricle to the left atrium as opposed to a healthy heart where this direction of flow is blocked by the mitral valve. The reverse flow during systolic causes a pressure rise in the left atrium. Maintaining a normal cardiac output results in an increased left ventricle pressure.

Treating patients with MR or TR (mitral regurgitation or tricuspid regurgitation) could require valve replacement in order to reduce or eliminate the regurgitation. For many years, the acceptable common treatment was surgical repair or replacement of the native valve during open heart surgery. In recent years, a trans-vascular technique has been developed for introducing and implanting a prosthetic heart valve using a flexible catheter in a manner that is less invasive than open heart surgery.

In the trans-vascular technique, the prosthetic is delivered to the target site (aortic valve, mitral valve, tricuspid valve, or other valve) through a catheter while the device is crimped to a low diameter shaft. When the prosthetic device is located in the correct position, it is expanded/deployed to a functional size.

Advancing the catheter to the target site can be through: (a) The vascular system, where a catheter is advanced from the femoral vein/artery, or any other blood vessel that allows access to the target site; (b) Trans-apically where a catheter is advanced through a small incision made in the chest wall and then through the apex; or (c) Trans-atrially where a catheter is advanced through a small incision made in the chest wall and then through the left or right atrium.

SUMMARY

A prosthesis secures a replacement valve in a heart. The prosthesis includes a radially expandable inflow section and outflow section and migration blocker rods. The inflow section has a tapered shape and is implanted within an atrium of a heart adjacent a native valve annulus. The outflow section couples to the inflow section and is configured to be implanted through the native valve annulus and at least partially within a ventricle of the heart. The migration blocker rods extend circumferentially around at least a portion of the outflow section and hold native leaflets of the heart valve. In a contracted configuration, the prosthesis may be implanted through a catheter into the heart. In an expanded configuration, the tapered shape of the inflow section in the atrium cooperates with the migration blockers in the ventricle to hold the prosthesis against the native valve annulus.

Additional aspects and advantages will be apparent from the following detailed description of preferred embodiments, which proceeds with reference to the accompanying drawings.

DETAILED DESCRIPTION OF PREFERRED EMBODIMENTS

When used the singular form "a", "an", "the" refers to one or more than one, unless the context clearly dictates otherwise.

As used herein, the term "includes" means "comprise" for example, a device that includes or comprises A and B contains A and B but can optionally contain C or other components other than A and B. A device that includes or comprises A and B may contain A or B, or A and B, and optionally one or more other components such as C.

Figure 3:
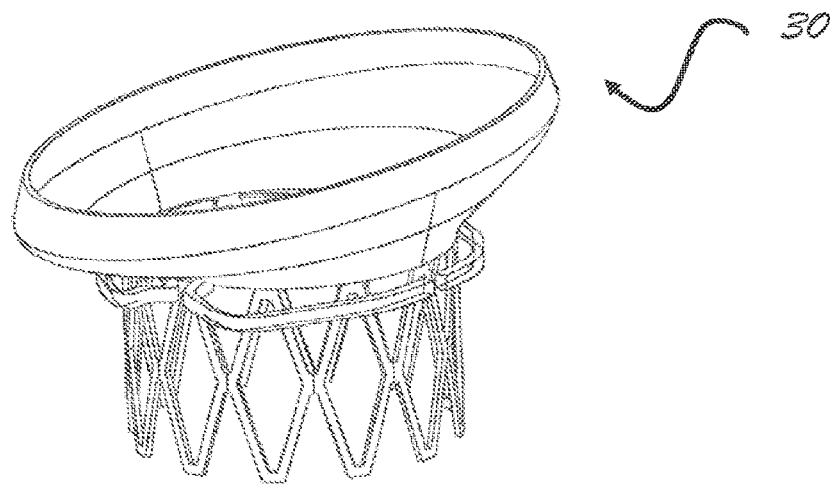
FIG. 3 is an isometric view of a stent configured for placement in a native mitral or tricuspid valve according to one embodiment.

When the words "stent" and "frame" are used they refer to the same element (e.g., see stent 30 in FIG. 3).

Figure 1A:
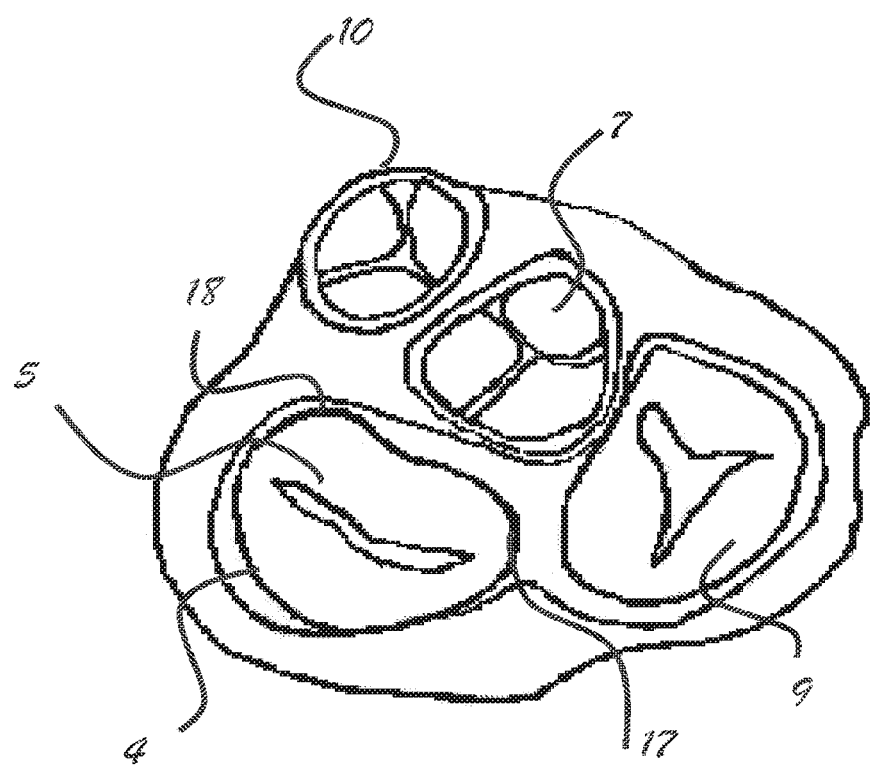
FIG. 1A illustrates a short axis view of a heart with four valves.
Figure 1B:
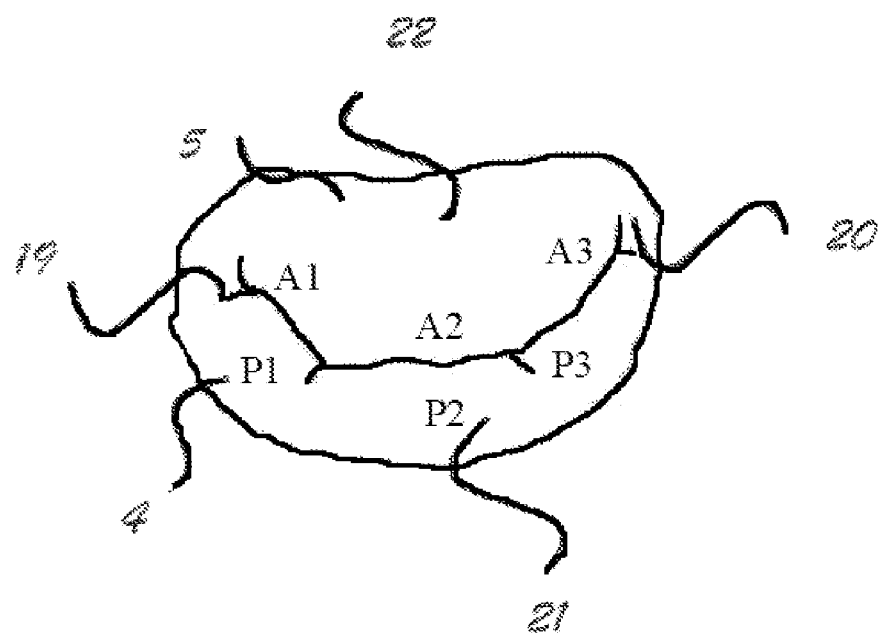
FIG. 1B illustrates a short axis view of mitral valve leaflets.

FIG. 1A shows a short axis section of the four valves in a heart: the aortic valve 7, pulmonary valve 10, tricuspid valve 9, and mitral valve with anterior leaflet 5 and posterior leaflet 4. In FIG. 1B, there is an illustration of the mitral valve with posterior leaflet 4 sectioned into P1, P2, P3 and anterior leaflet 5 sectioned into A1, A2, and A3. These sectioning methods are common knowledge and acceptable among those skilled in the art. FIG. 1B also shows a commissure 19 between A1 and P1 and a commissure 20 between A3 and P3.

Figure 2A:
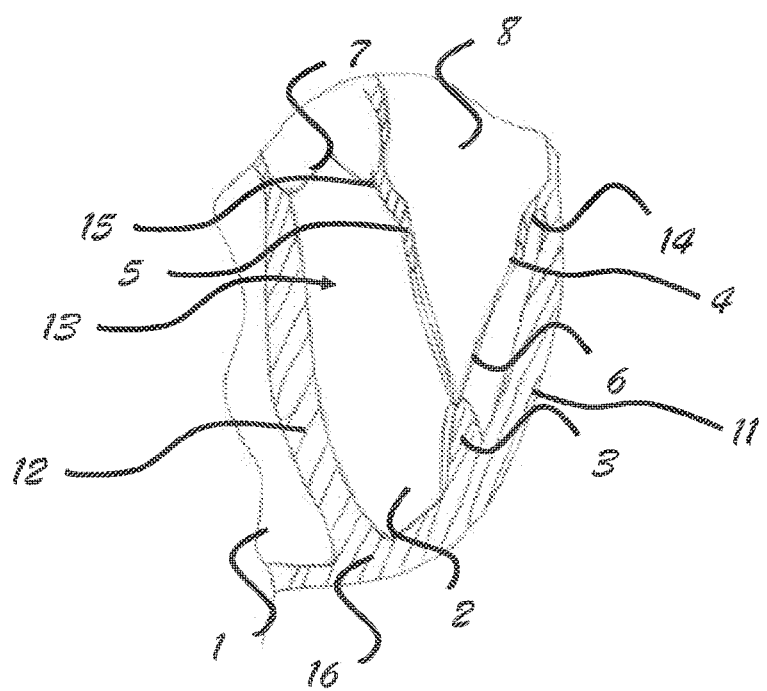
FIG. 2A illustrates a three-chamber view (long axis) of the heart.

FIG. 2A is a three chamber view (long axis) of the heart. In this view, the left atrium 8, left ventricle 2, and right ventricle 1 are shown. The aortic valve 7 is at the end of the left ventricle outflow tract (LVOT) 13. The mitral valve apparatus with mitral leaflets includes anterior leaflet 5 and posterior leaflet 4 attached to the chordae tandea 6 and papillary muscles 3. This view is a section of the mitral valve through the A2 (shown as area 22 in FIG. 1B) and P2 (shown as area 21 in FIG. 1B) areas of the mitral leaflets.

Figure 2B:
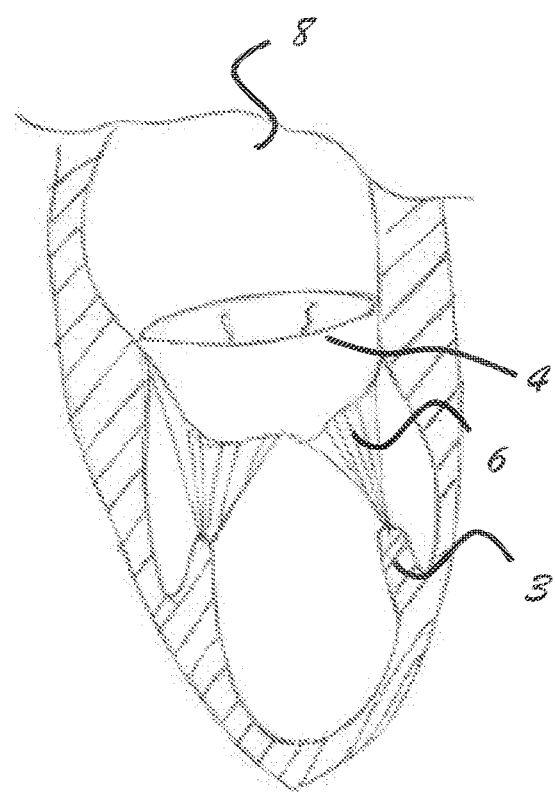
FIG. 2B illustrates a two-chamber view (long axis) of the heart.

FIG. 2B is a two chamber view (long axis) of the heart. In this view the left atrium 8 and left ventricle 2 are shown. The mitral valve apparatus includes the posterior mitral leaflet 4 attached to the chordae tandea 6 and papillary muscles 3. This view is a section of the mitral valve through the commissures 19 and 20 of the mitral leaflets.

Figure 4:
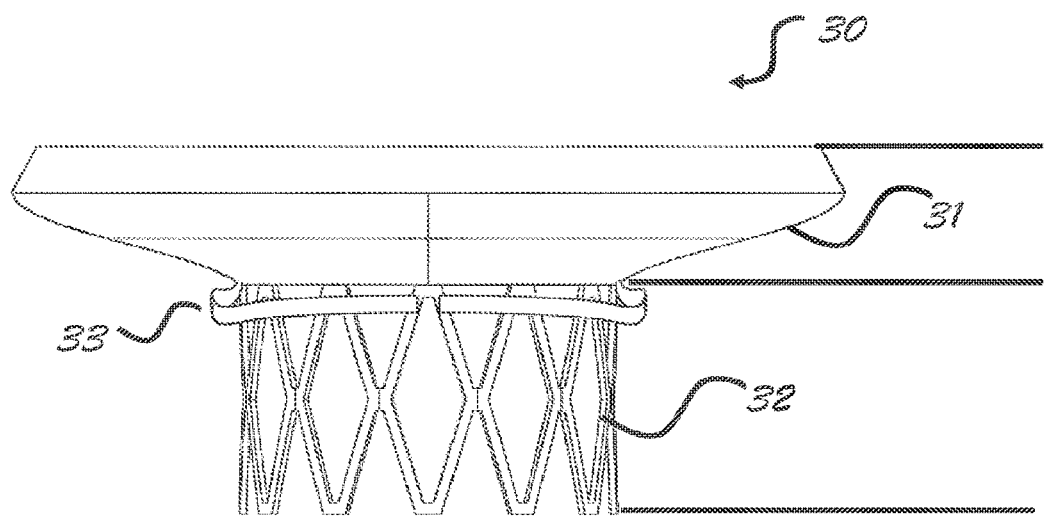
FIG. 4 is a front view of the stent shown in FIG. 3.

FIG. 3 is a perspective view of a stent 30 configured for placement in a native mitral or tricuspid valve. The stent 30 in FIG. 4 is a front view of the stent 30 shown in FIG. 3. In this embodiment, the stent 30 includes an upper section 31 (also referred to herein as "inflow section" 31) having an enlarged diameter (circumference) or flared end that tapers into a lower section 32 (also referred to herein as "outflow section" 32) of the frame having a reduced diameter (circumference). The upper section 31 and/or the lower section 32 may have different shape than circular. The stent 30 may have any combination of shapes FIGS. 5A-5H are only examples of the different shapes possible and other shapes may apply as well. Migration blocker rods 33 shown in FIGS. 3 and 4 are separated rods, which after deployment lean against the native annulus and prevent migration of the stent into the atrium 8 shown in FIG. 2A. The migration blocker rods 33 can have different lengths with different ends and additional features can be included, such as: A. a leading mechanism to ensure connectivity, after deployment, between different migration blocker rods; B. a locking mechanism between the rods; C. barbs to prevent rocking; and D. features that lock the migration blocker rods against the upper section 31 of the frame 30.

Inside the stent assembly, a prosthetic valve (not shown) may be added. The valve can be either bi-leaflet or tri-leaflet as long as it performs as required and can be made out of any tissue, polymer, or other material, as long as it is biocompatible. The stent 30 can be a self-expanding stent made of a shape memory material such as, for example, Nitinol. It can be cut from a tube, sheet, and/or a pattern that allows crimping and expanding like braided wires or any other technique that attaches wires.

In other embodiments, the stent 30 can be a combination of a self-expanding stent and a balloon expandable stent. For example, FIGS. 13A-13D demonstrate an upper section 31 including a shape memory alloy that functions as a self-expandable frame, and a lower section 32 including a balloon expandable stent that requires balloon inflation for final deployment. The two sections can be attached in any way. For example, welding, mechanical attachment (as shown in FIGS. 13A-13D), and/or additional features that attach them are only some of the ways to attach the two sections of the stent assembly.

The raw material of the stent 30 can be a metal of any kind that is biocompatible. The stent 30 may include a combination of two or more different materials. For example, the stent 30 may be one part stainless steel 316/316L and another part Nitinol. Other materials such as cobalt chrome may be used. The above materials are only examples, and other materials can be used as well.

The design of the frame 30, whether one part or more, is configured to allow crimping the prosthesis into a low profile shaft (equal to or less than 13 mm outer diameter (OD)). Patterns that allow this are known and crisscross patterns as shown for example in FIGS. 3 and 4 for the outflow section 32 or braided stents are two examples, and other patterns may be applied as well.

The migration blocker rods 33 of the stent 30 lean against the native annulus of the tricuspid or mitral valve, in general. When used in the mitral position, the migration blocker rods 33 may lean, in particular, against the mitral groove 14 shown in FIG. 2A in the posterior side and against the left fibrous trigon 18 and the right fibrous trigon 17 in the anterior side shown in FIG. 1A.

On the atrium side, the flared upper section 31 prevents any migration of the stent 30 into the ventricle 1 or 2 shown in FIG. 2A and helps provide sealing between the stent and the native apparatus by verifying good intimate contact and correlation between the inflow section geometry and the native shape of the mitral annulus and left atrium.

The combination of the migration blocker rods 33 from the ventricle side of the native annulus and the upper section 31 flared stent from the atrium side of the annulus create a clamping effect on the annulus and provide a positive axial anchoring of the stent 30 to its target site.

For the upper section 31, according to certain embodiments, an elliptical shape allows reducing the inflow section projection and therefore reduces the area that faces high pressure during systole. This feature reduces the axial forces that the prosthesis faces and needs to be anchored against. At the same time, an elliptical shape assures continuous contact between the upper section 31 and the atrium and prevents any para-valvular leakage (PVL). Any other shape that will at the same time prevent PVL and minimize the projection of the inflow may also be used.

Figure 9A:
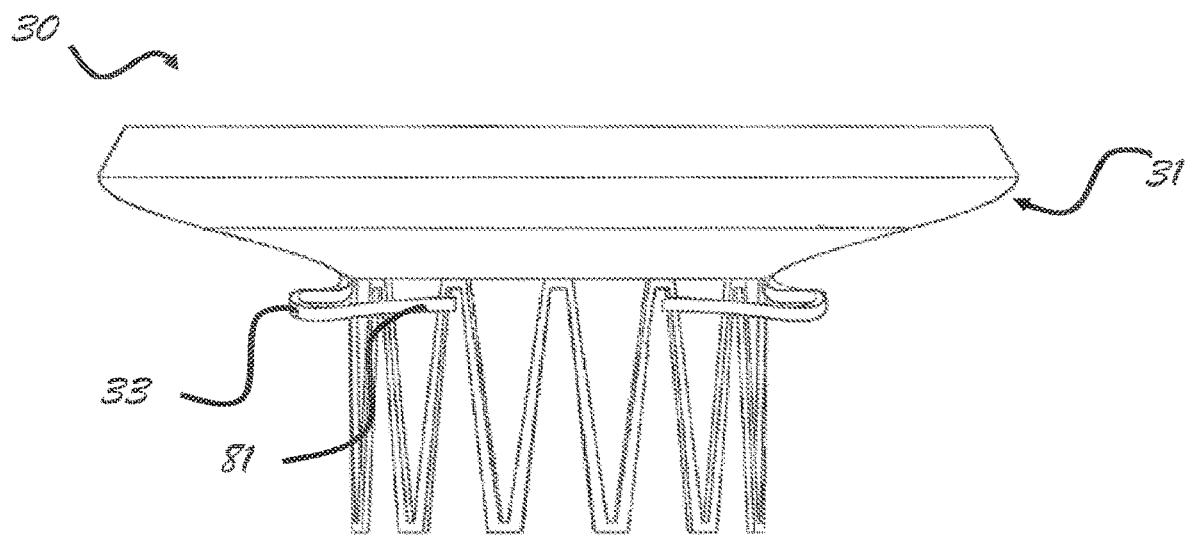
FIG. 9A is a front view of a stent illustrating a curvature of the inflow (high profile inflow) according to one embodiment.
Figure 9B:
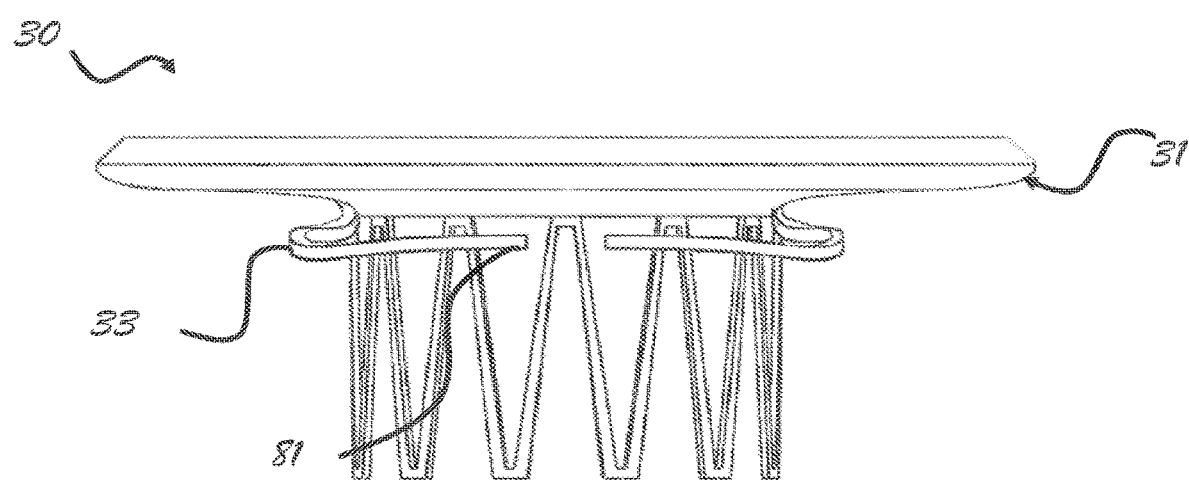
FIG. 9B is a front view of a stent illustrating a curvature of the inflow (low profile inflow) according to one embodiment.

The curvature that defines the transition zone and/or the inflow section profile may be configured to increase or decrease the clamping effect between migration blocker rods 33 and the inflow section 31. FIGS. 9A and 9B show two examples and any other curvature that allows the upper section to be fixated in the atrium and the migration blocker rods to stay under the native annulus in the ventricle is acceptable.

In the area of connection between the upper section 31 and lower section 32 of the stent 30 are attached migration blocker rods 33 which prevent the valve from migrating into the left atrium. The migration blocker rods 33 go in between the chordae under the native commissures 19 and 20 shown in FIG. 1B and lean against the mitral annulus from behind the native leaflets. FIGS. 14A, 14B, 15, 16A, 16B, and 17 show the extraction of the migration blocker rods from the stent, passing through the chordae and turning around the native leaflets. At the final position, the rods 33 lean against the native annulus.

FIGS. 5A-5H represents different combinations of the inflow and outflow profiles. The inflow profile in the illustrated embodiments can be either circular 57 (as shown in FIGS. 5C, 5D, 5G, and 5H) or elliptical 54 (as shown in FIGS. 5A, 5B, 5E, and 5F), or any other shape that fits the native anatomy of the atrium. The outflow profile can be either circular 58 (as shown in FIGS. 5A, 5B, 5C and 5D) or elliptical 59 (as shown in FIGS. 5E, 5F, 5G and 5H), or any other shape that fits to withhold a prosthetic valve inside, either bi leaflet or tri leaflet. FIGS. 5A-5H illustrate, by way of example, only four combinations out of many possible options for the design of the stent 30.

In FIGS. 5A-5H, the circumference of the inflow section 31 and its upper end 55 can vary between about 225 mm to 90 mm. This large variation is due to the target population of the device, which some have a very large atrium. The circumferences of the outflow section 32 and its lower end 56 can vary between about 110 mm to 60 mm. This variation is to allow different sizes of valves inside the outflow according to the acceptable standards, if they exist, for the mitral and tricuspid position. The height of the stent may vary between about 20 mm to 60 mm, as long as it doesn't injure the left ventricle walls by the lower section 32 and lower end 56 and doesn't interfere with the flow from the pulmonary veins and/or cause any risk relative to the left appendage. The valve 52 (shown in FIGS. 5A, 5C, 5F, and 5H) can be either bi-leaflet or tri-leaflet as long as it performs as required and can be made out of any tissue, polymer, or other material as long as it is biocompatible. The stent 30 can be a self-expanding stent made of a shape memory material such as, for example, Nitinol. It can be cut from a tube, sheet, and/or a pattern that allows crimping and expanding like braided wires or any other technique that attaches wires as long as it performs well.

Figure 5A:
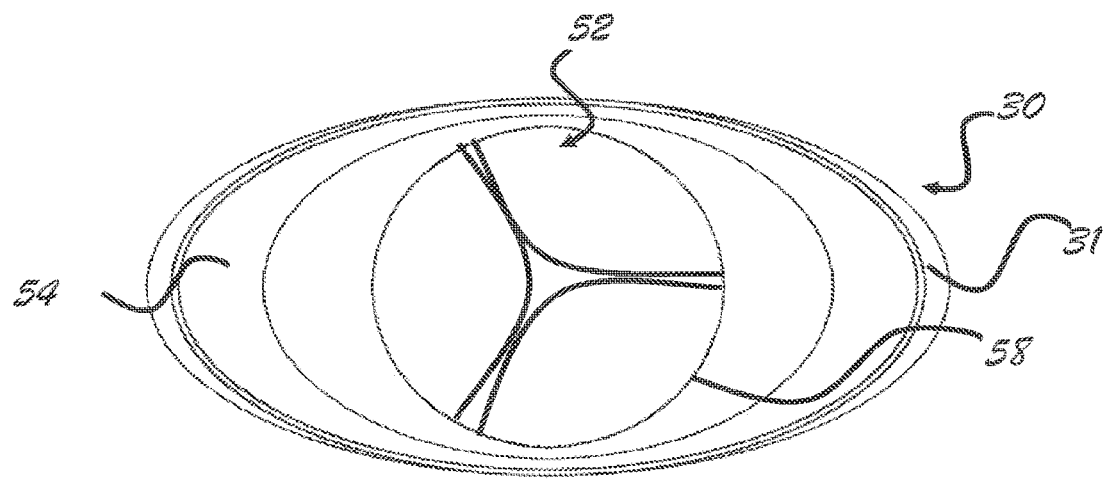
FIG. 5A is a top view of a stent with an elliptical inflow and circular outflow according to one embodiment.
Figure 5B:
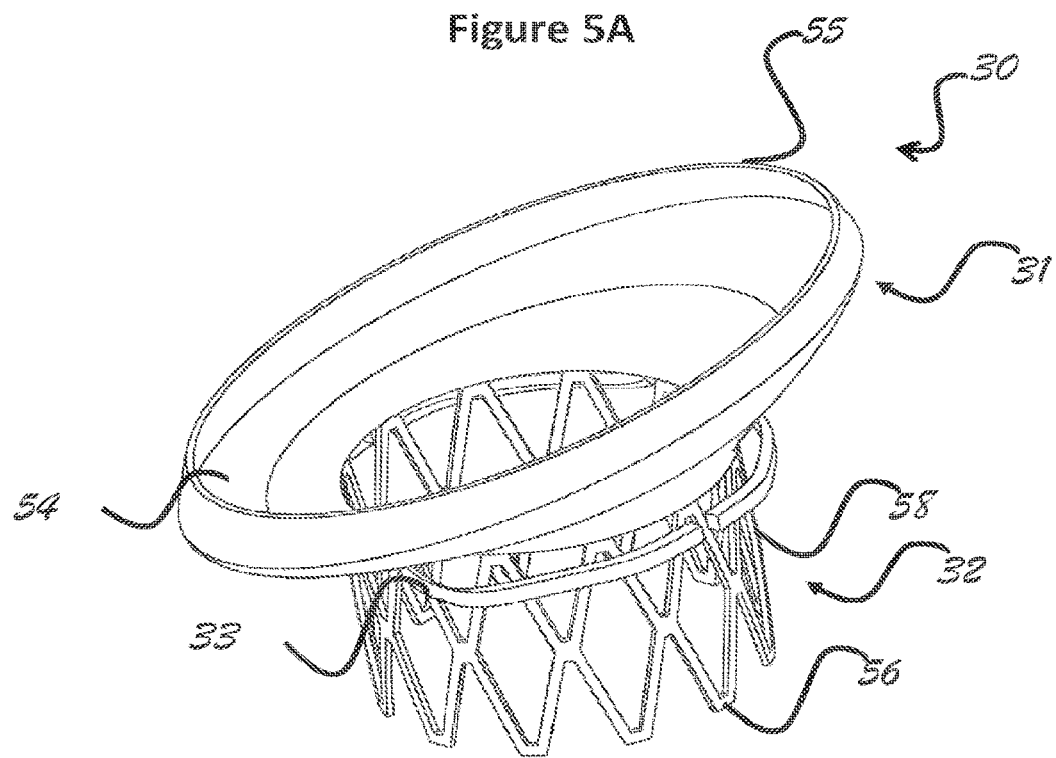
FIG. 5B is an isometric view of a stent with an elliptical inflow and a circular outflow according to one embodiment.
Figure 5C:
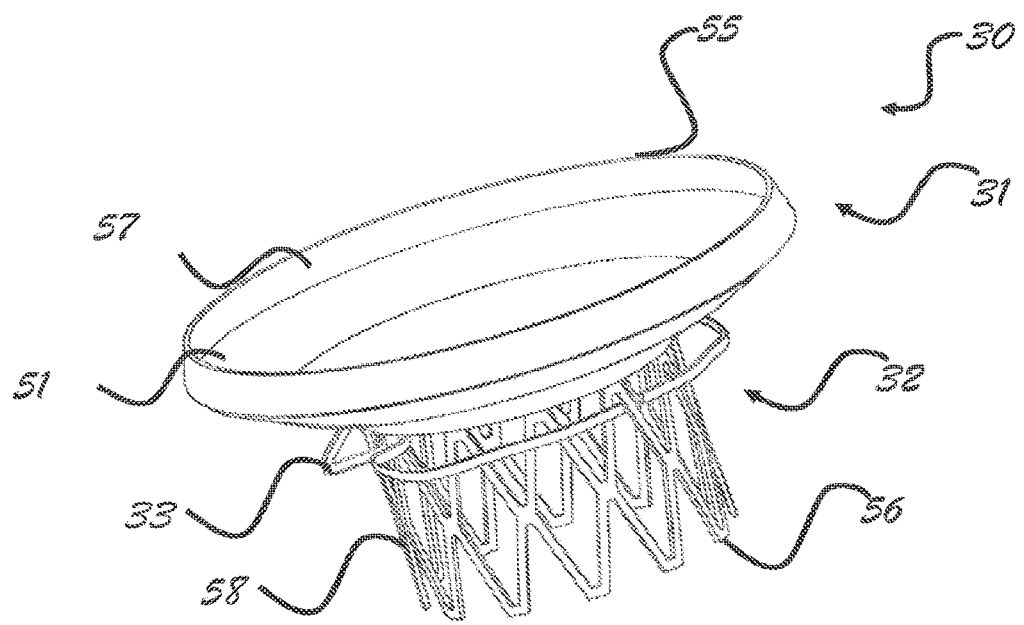
FIG. 5C is an isometric view of a stent with a circular inflow and a circular outflow according to one embodiment.
Figure 5D:
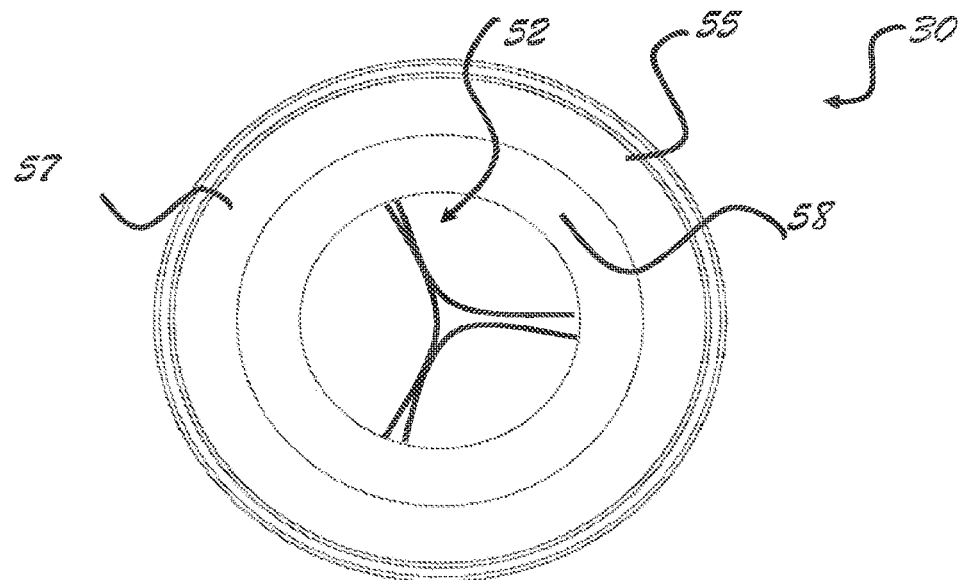
FIG. 5D is a top view of a stent with a circular inflow and a circular outflow according to one embodiment.
Figure 5E:
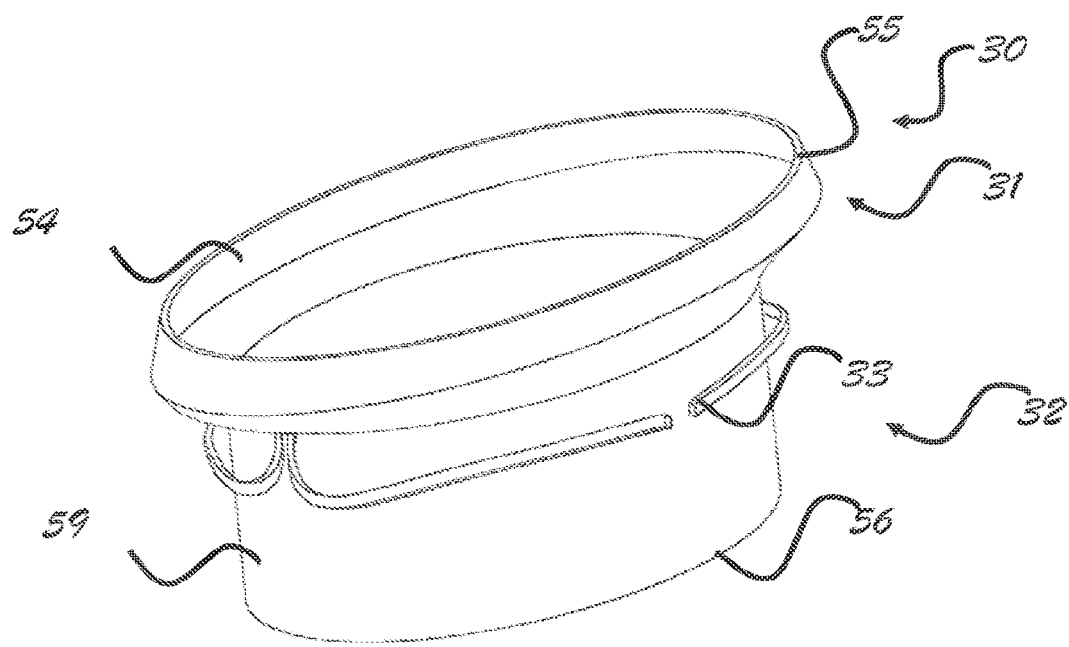
FIG. 5E is an isometric view of a stent with an elliptical inflow and an elliptical outflow according to one embodiment.

In FIGS. 5A and 5D, an illustrated tri leaflet valve 52 is mounted in the circular outflow section 32. The valve 52 is configured such that the flow of blood goes substantially only in one direction and that substantially no back flow will occur through the valve according to the acceptable standards.

The valve 52 can be composed from biological tissue such as pericardium or alternatively from a polymer, fabric, or the like.

Figure 5F:
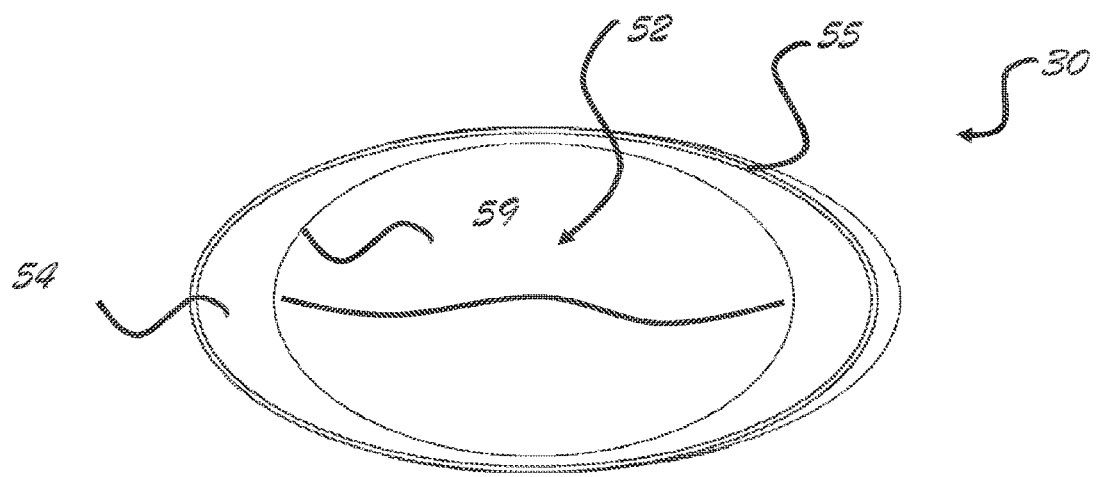
FIG. 5F is a top view of a stent with an elliptical inflow and an elliptical outflow according to one embodiment.
Figure 5G:
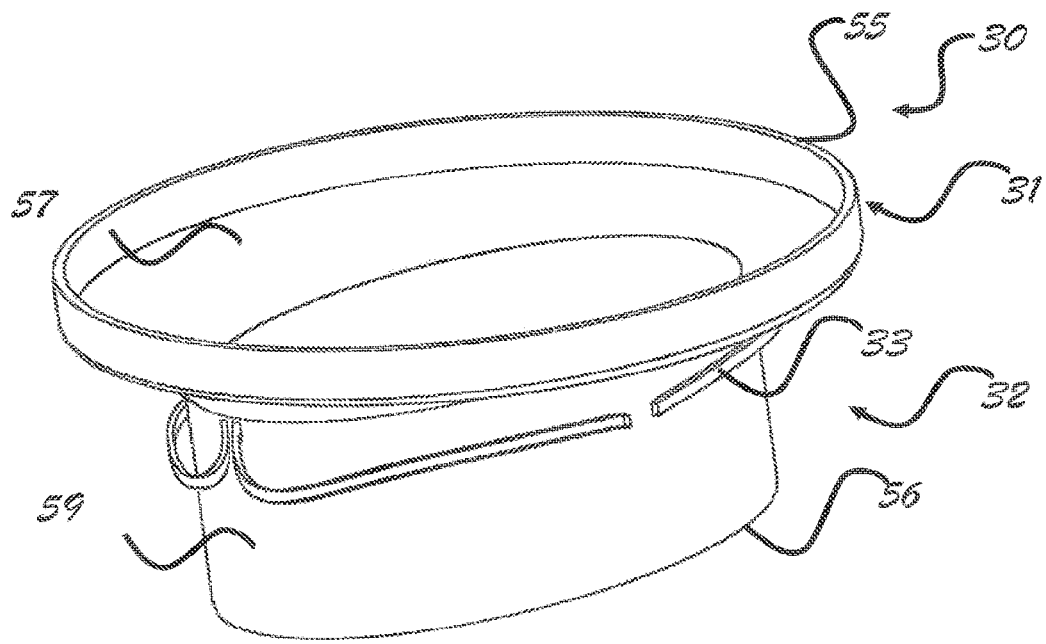
FIG. 5G is an isometric view of a stent with a circular inflow and an elliptical outflow according to one embodiment.
Figure 5H:
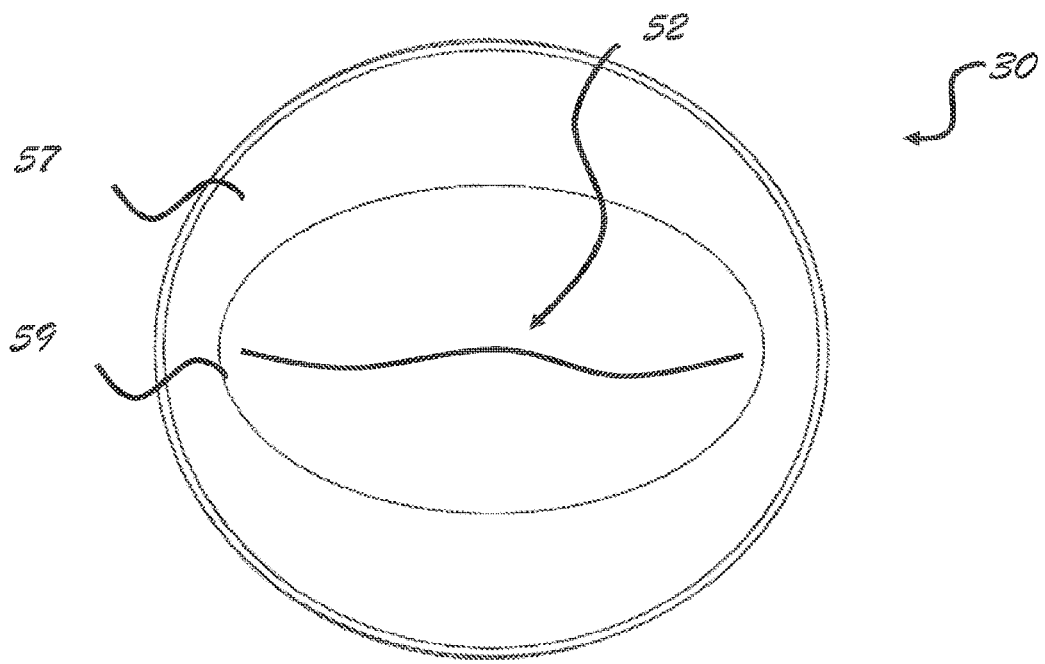
FIG. 5H is a top view of a stent with a circular inflow and an elliptical outflow according to one embodiment.

In other embodiments, such as shown in the FIGS. 5F and 5H, the valve 52 in the outflow section 32 can be bi leaflet.

Figure 6A:
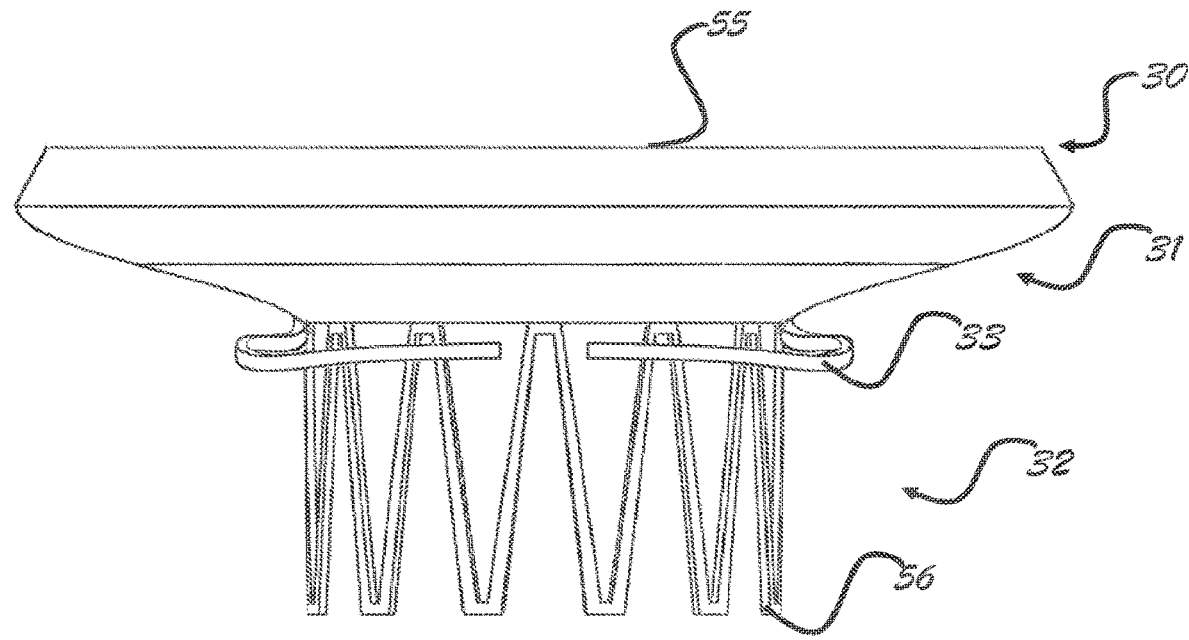
FIG. 6A is a front view of a stent having an outflow with one row of struts according to one embodiment.
Figure 6B:
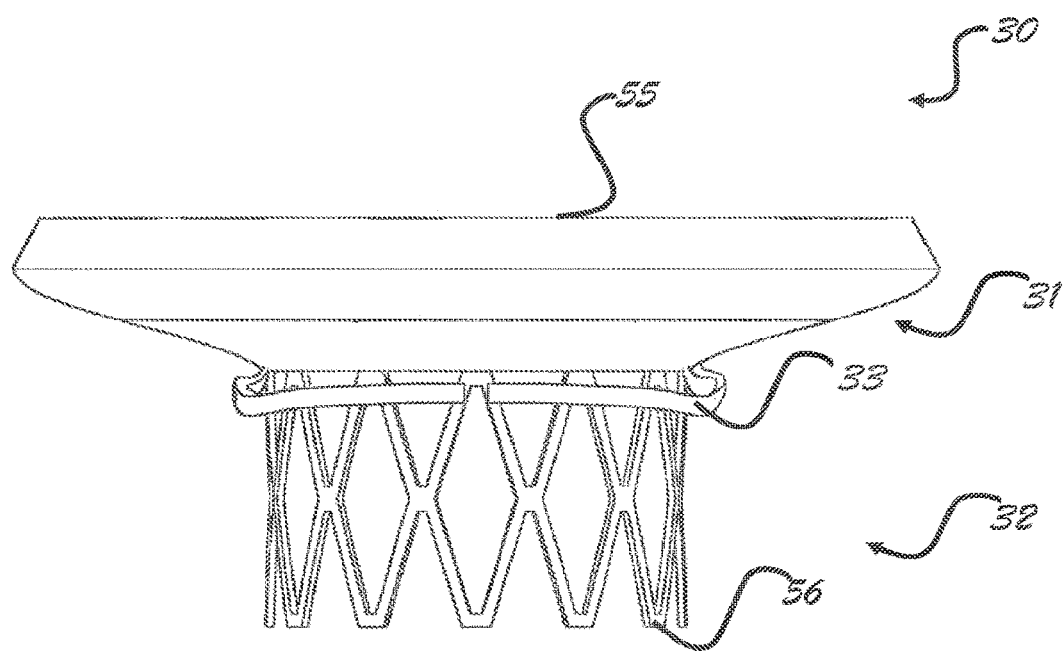
FIG. 6B is a front view of a stent having an outflow with two rows of struts according to one embodiment.

In FIGS. 6A and 6B, there is a front view of the stent 30 according to certain embodiments. It is illustrated as an example that the stent 30 can have any number of rows of struts (illustrated as "V" shaped structural supports), as long as the struts allow crimping into a catheter and deployment to the final configuration. The outflow section 32 can have either 1 (one) row of struts or more. In the illustrated embodiments, there is an example of an outflow section 32 with 1 (one) row of struts in FIG. 6A, and an embodiment of an outflow section 32 with 2 (two) rows of struts in FIG. 6B. This is not limiting and more rows can be added. In certain embodiments, the inflow section 31 also includes expandable struts. For example, the inflow section 31 may be designed in a similar manner as that of the outflow section 32 with a criss-cross pattern and/or any number of rows of struts, as long as the expandable struts allow crimping and expanding of the inflow section 31 to its different configurations.

Figure 7A:
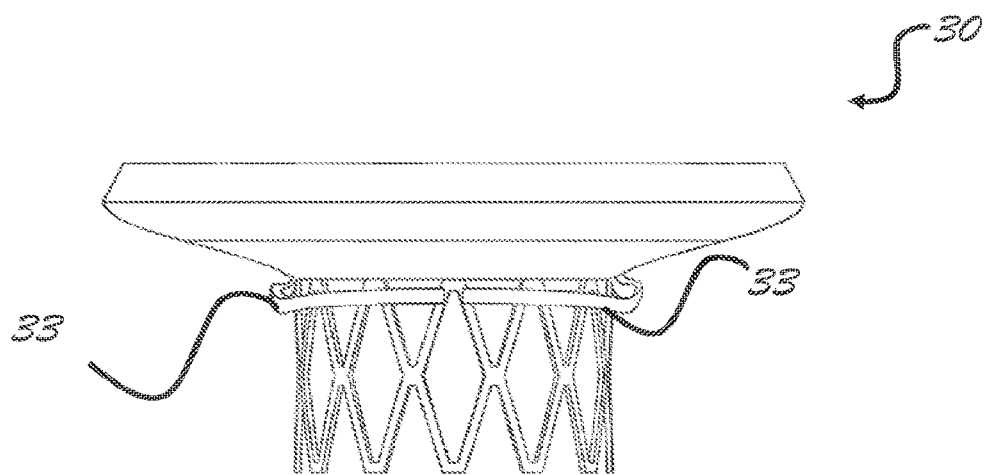
FIG. 7A is a front view of migration blocking rods of a stent according to one embodiment.
Figure 7B:
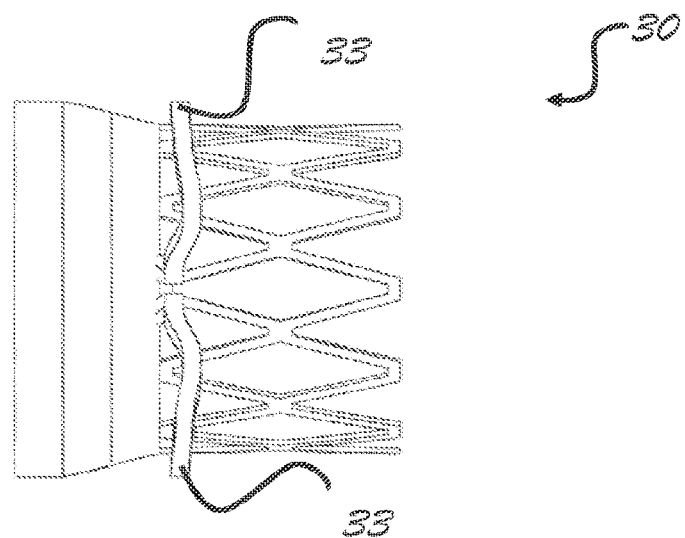
FIG. 7B is a side view of the migration blocking rods of the stent shown in FIG. 7A.
Figure 7C:
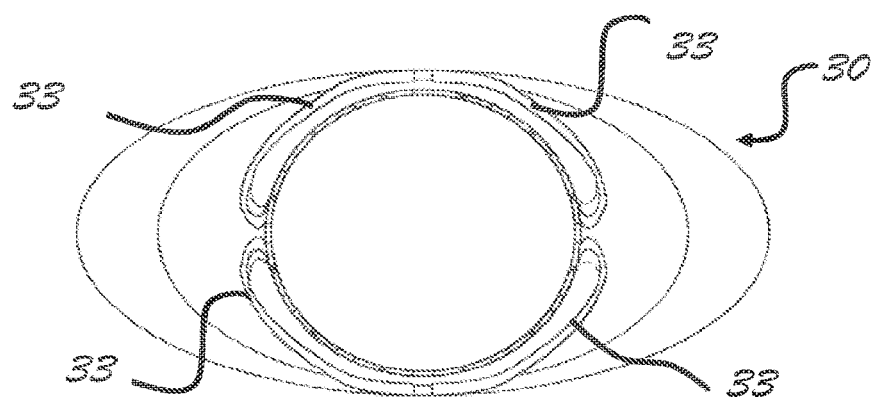
FIG. 7C is a bottom view of the migration blocking rods of the stent shown in FIG. 7A.

FIGS. 7A, 7B, and 7C illustrate the migration blocker rods 33 from three different views. FIG. 7A illustrates the migration blocker rods 33 in stent 30 from a front view, FIG. 7B illustrates the migration blocker rods 33 in stent 30 from a side view, and FIG. 7C illustrates the migration blocker rods 33 in stent 30 from a bottom view. The rods 33 are configured to be attached to the stent 30 either to the inflow section 31 or to the outflow section 32 at the area where these sections are attached to each other, and to provide axial fixation of the stent 30 at the target site.

The migration blocker rods 33 around the posterior leaflet 4 are configured to lean against the mitral groove 14 and prevent any migration and axial movement in the posterior side.

The migration blocker rods 33 around the anterior leaflet 5 are configured to lean against the left and right fibrous trigons 17 and 18 and prevent any migration and axial movement in the anterior side.

There are one, two, or more migration blocker rods 33 around the posterior leaflet 4. There are another one, two, or more migration blocker rods 33 around the anterior leaflet 5. The quantity of the migration blockers can vary from two to multiple rods and in the certain illustrated embodiments there are four of them only for visualization and as example. In other embodiments, the quantity of migration blocker rods 33 can be any number from two to eighteen.

The migration blocker rods 33 can have ends separated from one another, can meet each other behind the leaflets 4 and 5, may include a leading mechanism behind the leaflet to ensure the attachment of the rods to one another and may include a locking mechanism that prevents them from separating after deployment.

Figure 8A:
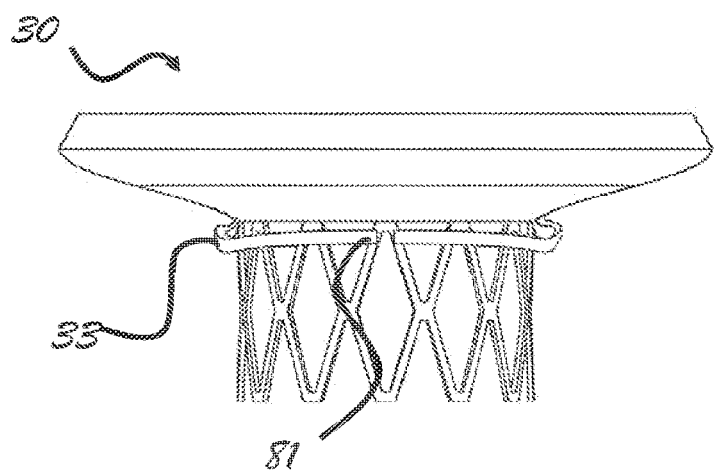
FIG. 8A is a front view of migration blocking rods with ends close to each other according to one embodiment.
Figure 8B:
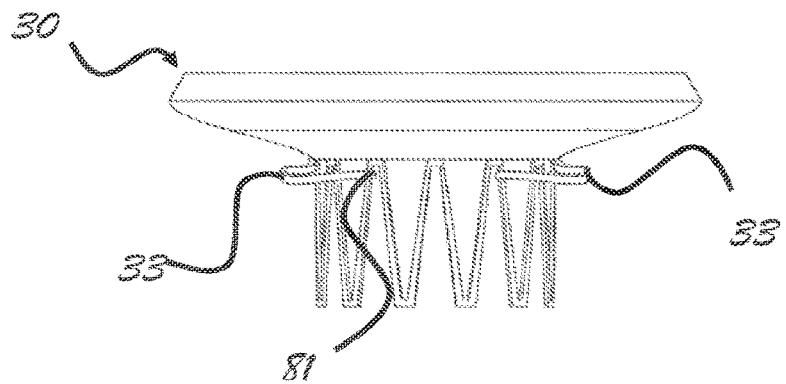
FIG. 8B is a front view of migration blocking rods with ends far from each other according to one embodiment.

The migration blocker rods 33 can be in different lengths with different ends 81 and additional features can be added on them. The ends 81 of the migration blocker rods 33 can be seen in FIGS. 8A and 8B. It can be seen that the distance between them can vary from zero, at minimum (they can touch each other), to, at maximum, half the circumference of the outflow section. In the later, the length of the rods 33 is very short and the point of leaning against the annulus is under the commissures 19 and 20 in FIG. 1B.

Figure 10A:
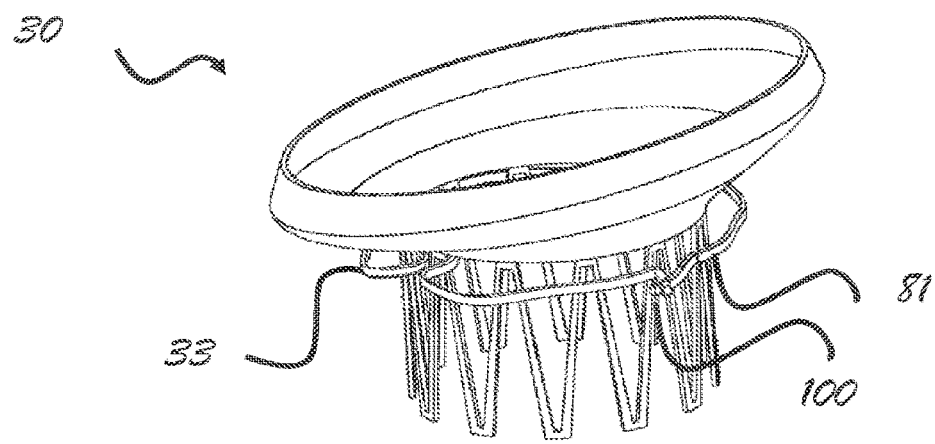
FIG. 10A is an isometric view of a stent including migration rods with a leading mechanism at the distal end according to one embodiment.
Figure 10B:
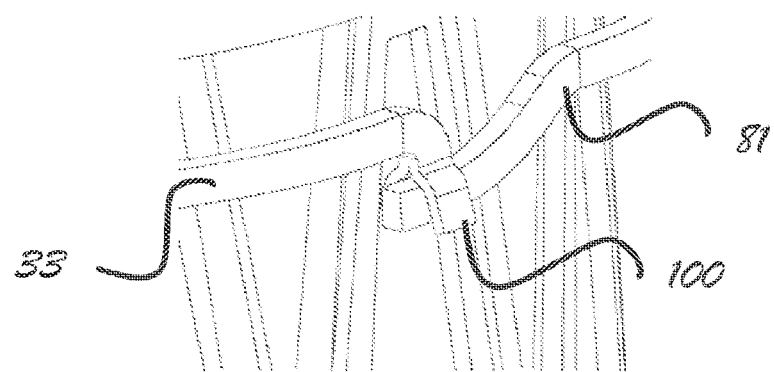
FIG. 10B is an enlarged view of the leading mechanism at the distal end of the migration blocking rods shown in FIG. 10A.

In FIGS. 10A and 10B, there is a leading mechanism 100 at the end 81 of the migration blocker rods 33 that allows connecting two migration blocker rods 33 that come from opposite commissures 19 and 20. The leading mechanism 100 allows two different migration blocker rods 33 to meet and attach to each other. Due to the nature of beating heart procedures and no direct visualization (only through X-ray and ultrasound), it may be useful to have such a mechanism 100 that allows leading one rod 33 into the other to assure that the two can be connected. The illustrated mechanism 100 is only one example. Others can be designed and might include wire, suture, metallic, and/or plastic members, etc.

Figure 11A:
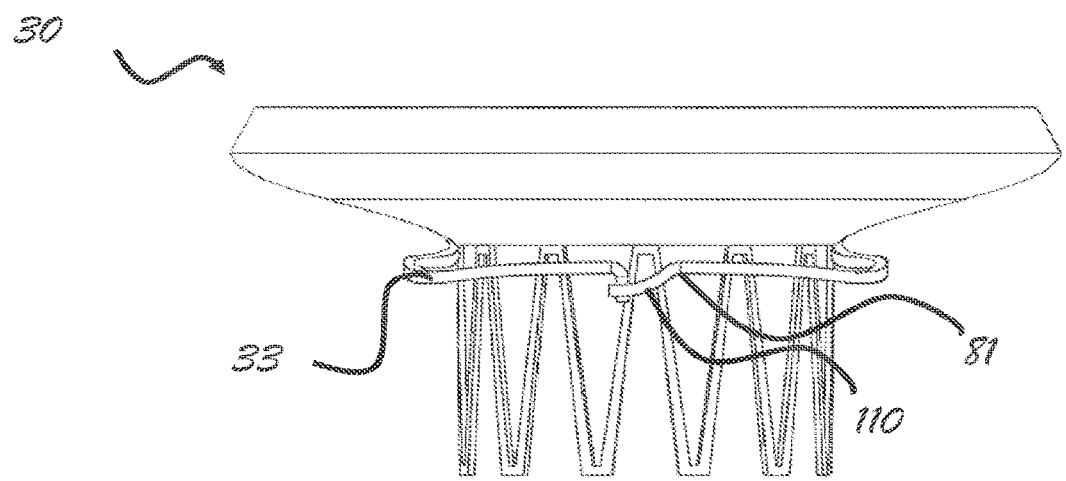
FIG. 11A is a front view of a stent including a migration locking mechanism with snapping according to one embodiment.
Figure 11B:
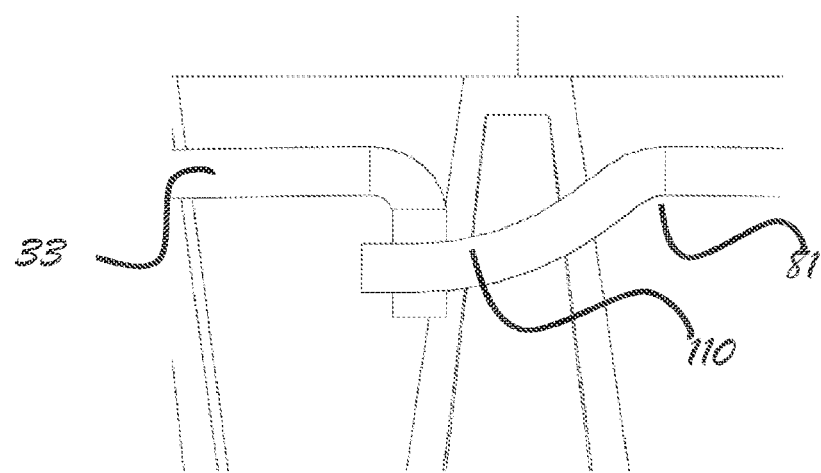
FIG. 11B is an enlarged view of the migration locking mechanism with snapping shown in FIG. 11A.
Figure 11C:
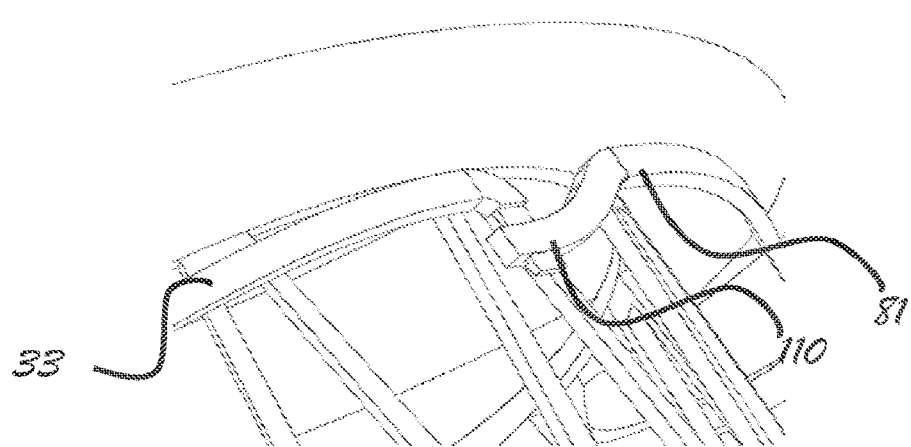
FIG. 11C is an isometric enlarged view of the migration locking mechanism with snapping shown in FIG. 11A.

In FIGS. 11A, 11B, and 11C, there is a snapping mechanism 110 at the end 81 of the migration blocker rods 33 that allows connecting two migration blocker rods 33 that come from opposite commissures 19 and 20 and lock them one into the other. Once two migration blocker rods 33 are attached and locked the stent is firmly secured in place and the rods 33 can't be crimped back to the crimped configuration unless the snap mechanism 110 is released. The snap illustrated in FIGS. 11A, 11B, and 11C is one example for such mechanism and others with additional members as metallic and/or plastic parts, wire, suture can be added.

Figure 12A:
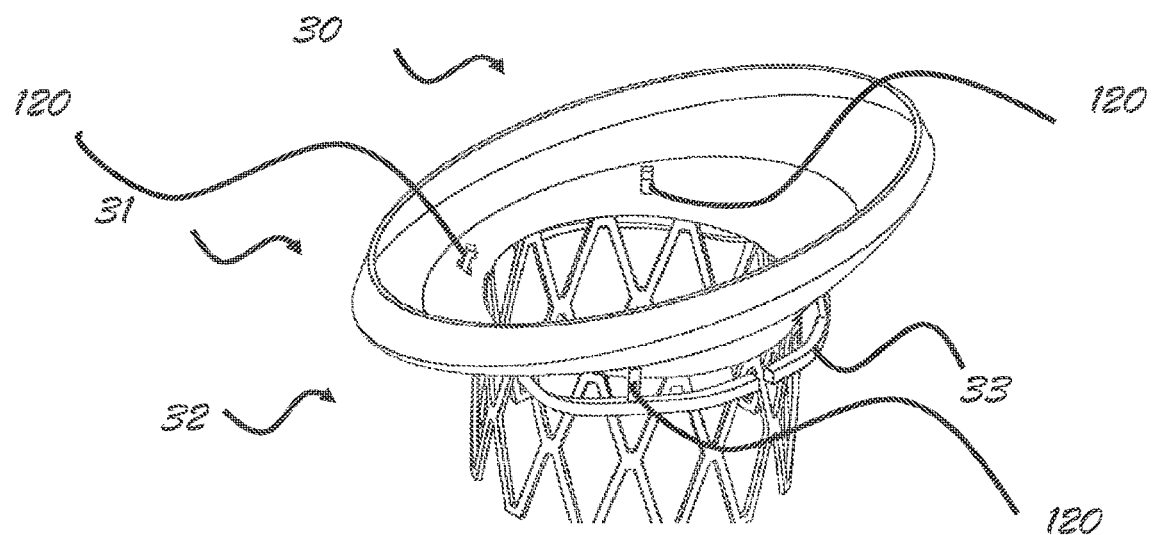
FIG. 12A is an isometric view of a stent including barbs extending from the inflow section according to one embodiment.
Figure 12B:
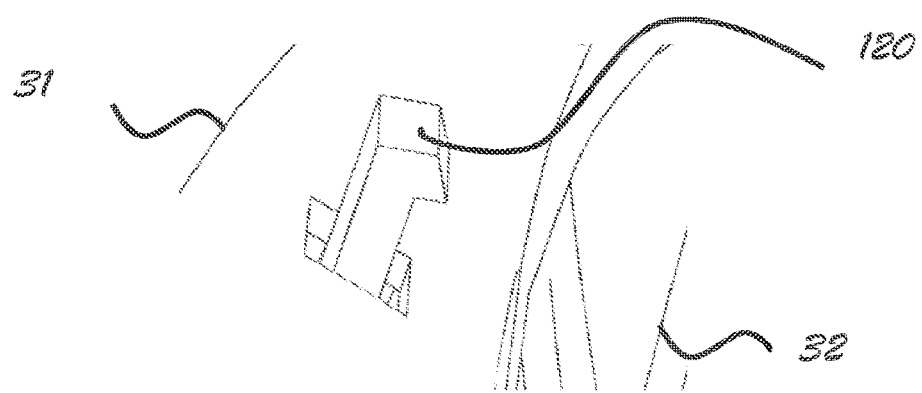
FIG. 12B is an enlarged view of a barb shown in FIG. 12A.

FIGS. 12A and 12B illustrate migration blocker rods 33 that include barbs 120 configured to penetrate the mitral annulus from the ventricle side and ensure no relative movement between the frame 30 and the mitral annulus. The barbs 120 that penetrated the mitral annulus can be locked into the inflow section of the frame from the atrium side or locked into an additional ring. FIG. 12B is a zoom on the isometric view of a barb that is part of a migration blocker rod 33 that penetrated through the annulus into the inflow section 31.

The migration blocker rods 33 can be cut from the same tube and heat treated to the final shape. The migration blocker rods 33 can be cut from different tube and be attached to the main frame differently using a direct attachment such as welding or with additional members such as sutures, metallic parts, etc. The migration blocker rods 33 can be crimped distally to the main frame, proximally to the main frame and on top of it. The migration blocker rods 33 might be covered with a fabric, soft tissue, and/or polymer to prevent any damage to the annulus apparatus.

FIGS. 13A, 13B, 13C and 13D illustrate a stent 30 that includes two different sections. The inflow section 31 is a self-expanding stent made from a shape memory alloy and functions as a self-expandable frame, and the outflow section 32 is a balloon expandable stent that requires balloon inflation for final deployment.

Figure 13A:
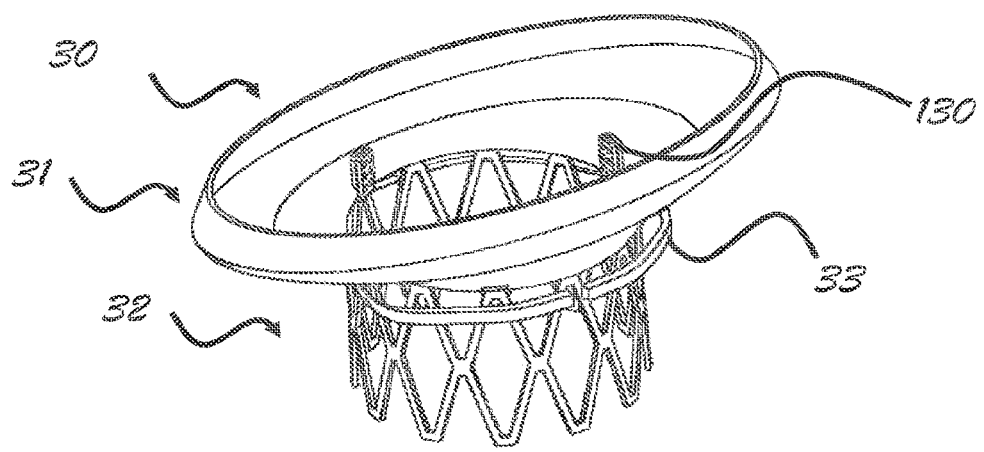
FIG. 13A is an isometric view of a stent including separate inflow and outflow sections according to one embodiment.

FIG. 13A is an isometric view of the two sections attached together through an attachment member 130. The attachment member 130 can be part of the inflow section 31, outflow section 32, both the inflow section 31 and the outflow section 32, and/or as an additional member.

Figure 13B:
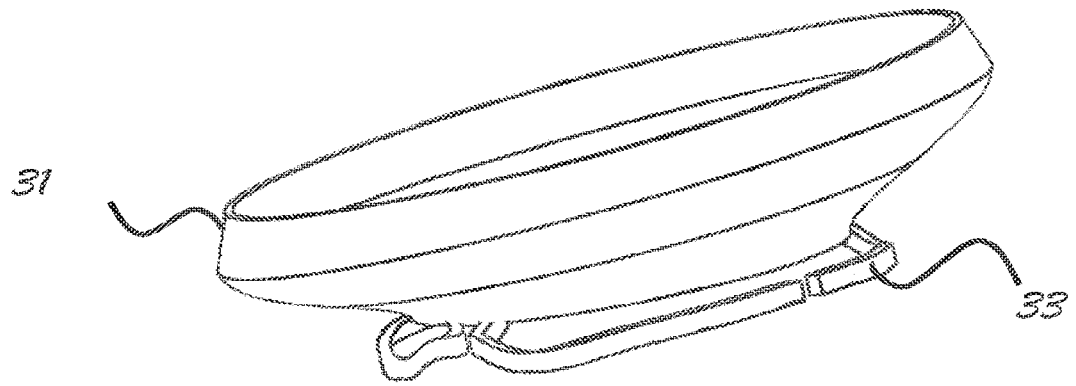
FIG. 13B is an isometric view of the separated inflow section shown in FIG. 13A.

FIG. 13B illustrates an example of an inflow section 31 made out of shape memory alloy where the migration blocker rods 33 are part of it. For example, inflow section 31 and the migration blocker rods 33 may be formed from the same piece of shape memory material. In other embodiments of the inflow section 31, the migration blocker rods 33 can be omitted or designed differently. In addition or in other embodiments of the inflow section 31, an attachment feature for connecting to the outflow section 32 can be added. An example of such a feature is a metallic flange that is cut from the frame and illustrated in the attached embodiments as attachment member 130.

Figure 13C:
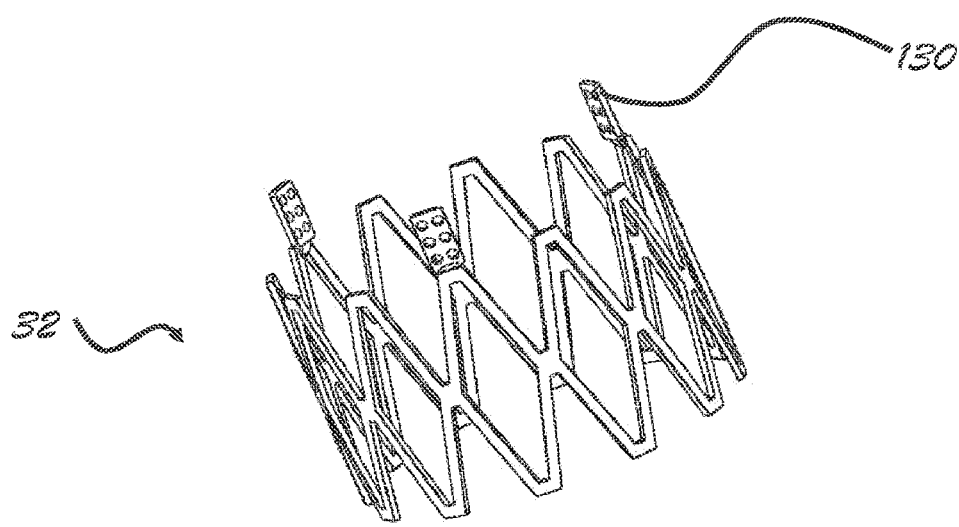
FIG. 13C is an isometric view of the separated outflow section shown in FIG. 13A.

FIG. 13C illustrates an example of an outflow section 32 made out of an alloy such as stainless steel (StSt), such as StSt 316/StSt 316L. In other embodiments, the outflow section 32 can be made out of a self-expandable alloy, such as, a shape memory alloy, and might include the migration blocker rods 33. In addition or in other embodiments of the outflow section 32, an attachment feature for connecting to the inflow section 31 can be added. An example of such a feature is a metallic flange that is cut from the frame and illustrated in the attached embodiments as attachment member 130.

Figure 13D:
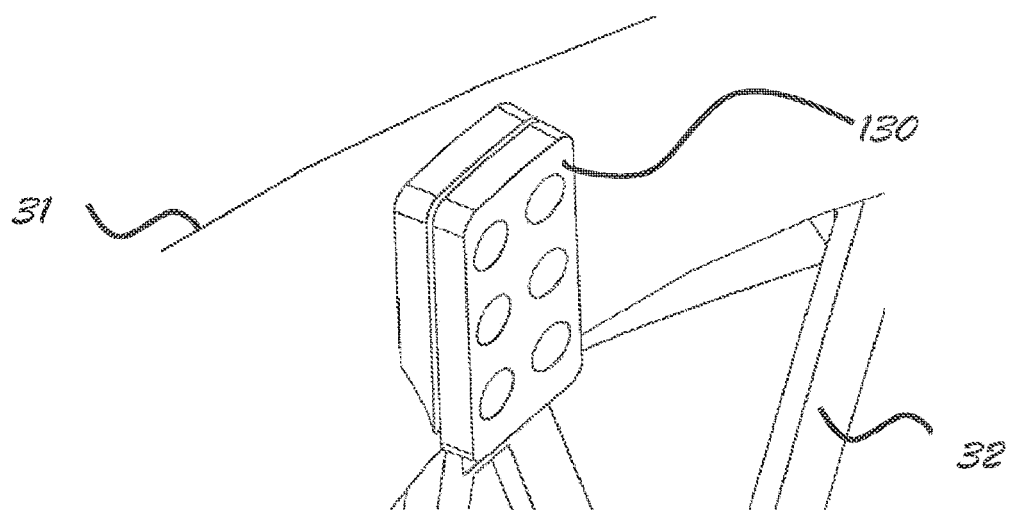
FIG. 13D is an enlarged isometric view of a connection area of the inflow and outflow sections shown in FIG. 13A.

FIG. 13D illustrates an enlarged view of the attachment feature 130 between the inflow section 31 and the outflow section 32. In this embodiment, the attachment feature 130 includes two metallic flanges. One is part of the inflow section 31, and one is part of the outflow section 32. The two flanges can be attached together by snapping one to another, suturing them together, or any other attachment method.

Figure 14A:
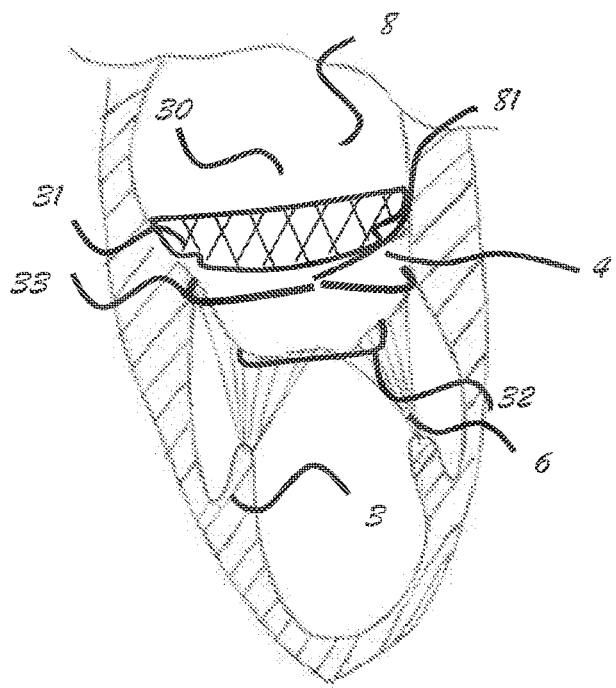
FIG. 14A illustrates a stent inside a heart in a three chamber view according to one embodiment.
Figure 14B:
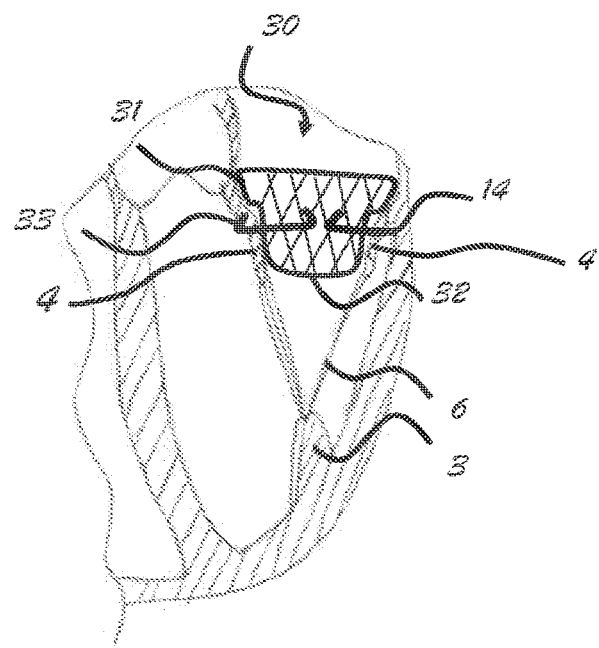
FIG. 14B illustrates a stent inside a heart in a three chamber view according to one embodiment.

FIGS. 14A and 14B illustrate how the stent 30 may be positioned in the mitral valve. In FIG. 14A, the section of the heart illustrates a two chamber view and the cross-section of the drawing passes through the mitral valve commissures. It can be seen that the stent 30 is behind the posterior leaflet 4, the migration blocker rods 33 pop out from the commissures 19 and 20, and the end 81 of the migration blocker rods 33 is in the P2 section of the leaflet (area 21 in FIG. 1B). In FIG. 14B, the section of the heart illustrates a three chamber view and the cross-section of the drawing passes through the A2 and P2 (areas 21 and 22 in FIG. 1B) of the native valve. It can be seen that the stent 30 is between the posterior leaflet 4 and anterior leaflet 5, the migration blocker rods 33 pop out from the commissures area, and the ends 81 of the migration blocker rods 33 are located in the posterior side under the mitral groove 14 and under the left and right fibrous trigons (18 and 17 in FIG. 1A) in the anterior side.

Figure 15:
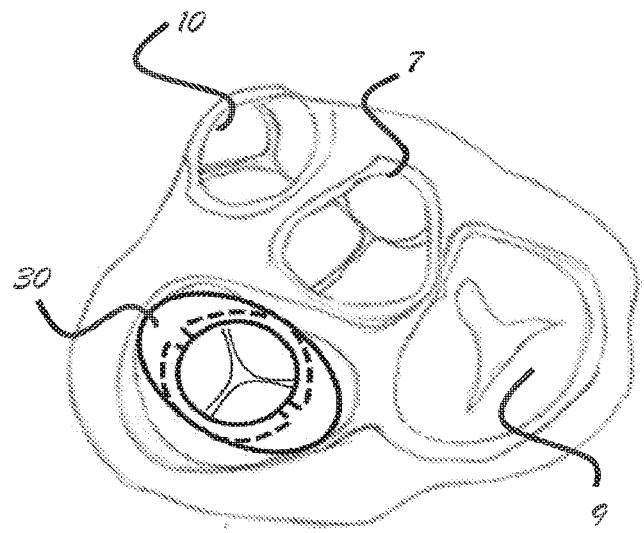
FIG. 15 is a short axis view of a heart with a stent implanted therein according to one embodiment.

FIG. 15 illustrates the stent 30 in the mitral valve from a short axis view from the atrial side. The migration blocker rods 33 are located in the ventricle side under the mitral leaflets.

Figure 16A:
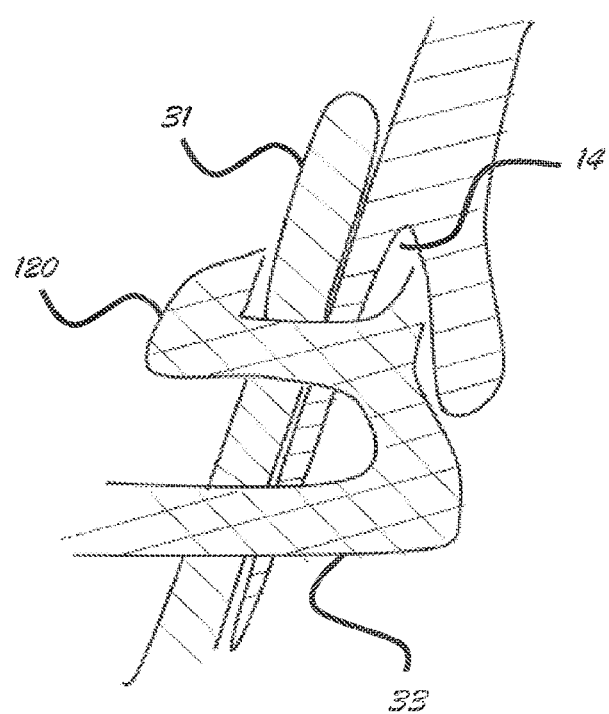
FIG. 16A is an enlarged view of a barb shown in FIG. 16B according to one embodiment.
Figure 16B:
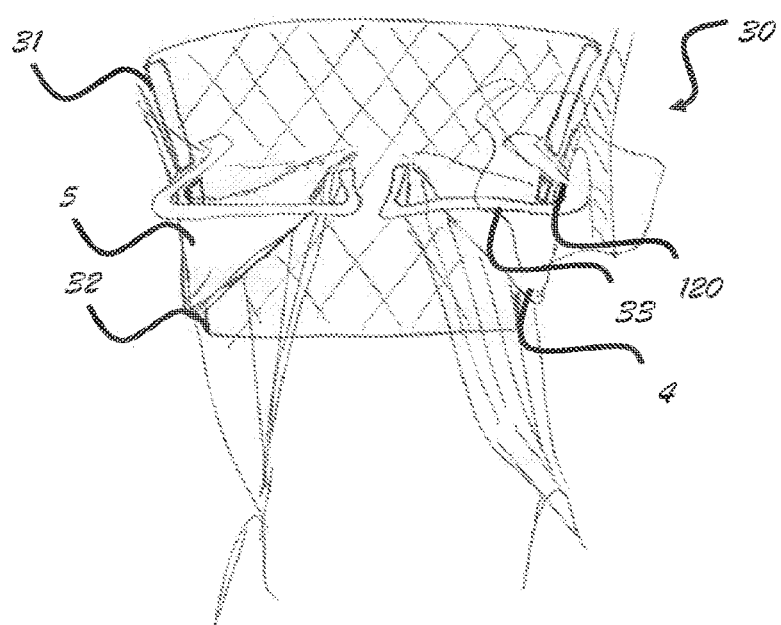
FIG. 16B illustrates a locking mechanism between the migration blocker rods and the inlet according to one embodiment.

FIGS. 16A and 16B illustrate an additional feature that can be added to the migration blocker rods 33. The barbs 120 are part of the migration blocker rods 33 and are designed in a way that after deployment they penetrate the mitral annulus and/or mitral leaflets and anchor the stent to the annulus. The barbs 120 can be an integral part of the migration blocker rods 33 or an additional member that is assembled on the barbs. The barbs 120 may be configured so that they have an opposite member or feature in the inflow section 31 in a way that after crossing the tissue they lock into the inflow section.

Figure 17:
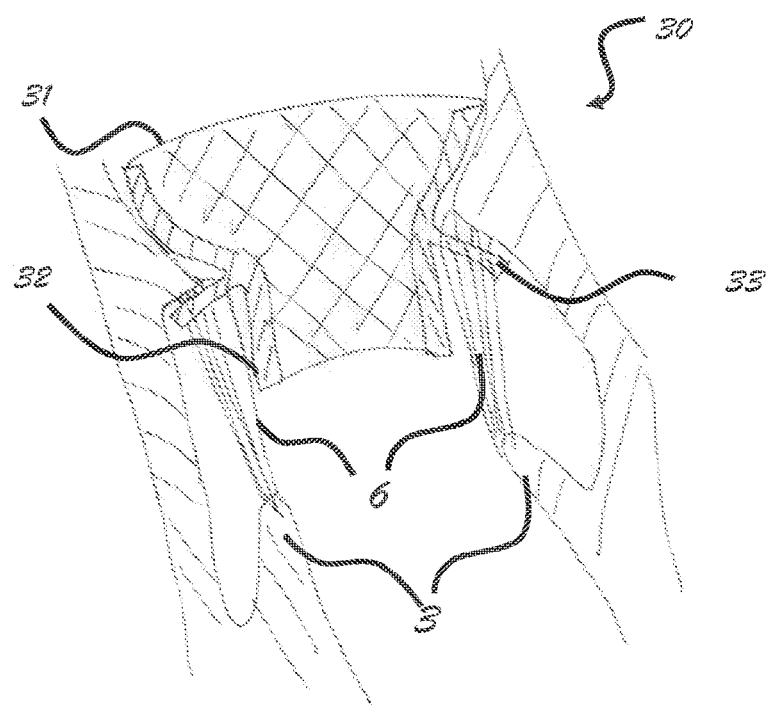
FIG. 17 is a detailed cross-section view of migration blocker rods passing through the chordae according to one embodiment.

FIG. 17 is an additional illustration that shows how the migration blocker rods 33 pass between the chordae tandea 6 in the commissures 19 and 20.

Figure 18:
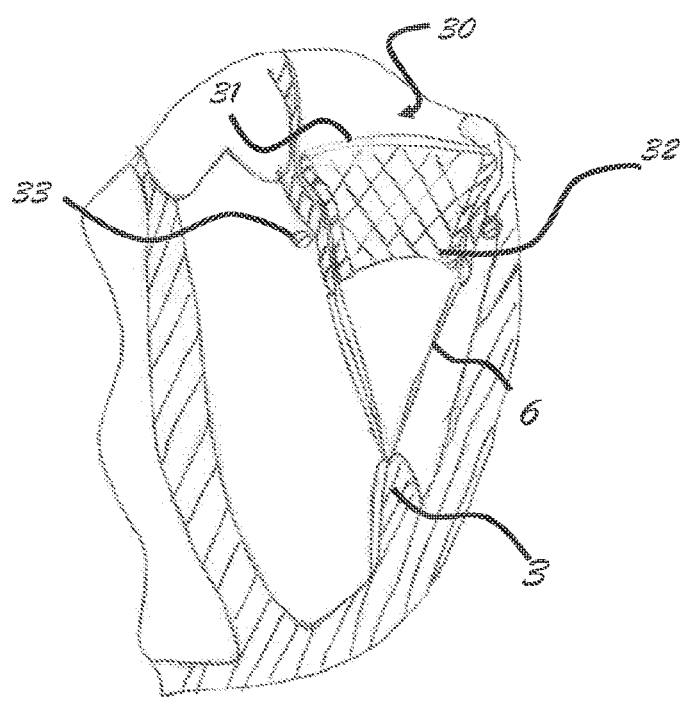
FIG. 18 is a detailed cross-section view of a stent inside a heart, from a septal lateral perspective, according to one embodiment.

FIG. 18 is an additional drawing illustrating how the migration blocker rod 33 leans against the mitral groove 14 in the posterior side and the left and right fibrous trigons on the anterior side.

Figure 19A:
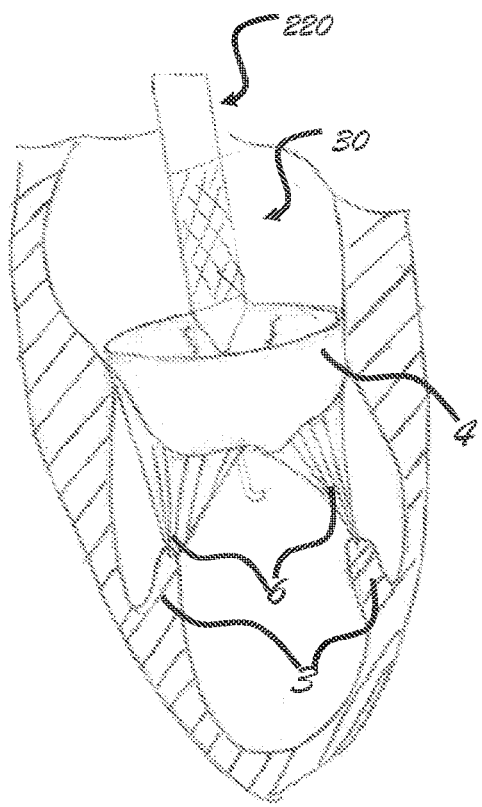
FIGS. 19A, 19B, 20, and 21 show an example of a trans atrial approach for trans catheter implantation of a stent in the mitral position according to one embodiment.
Figure 19B:
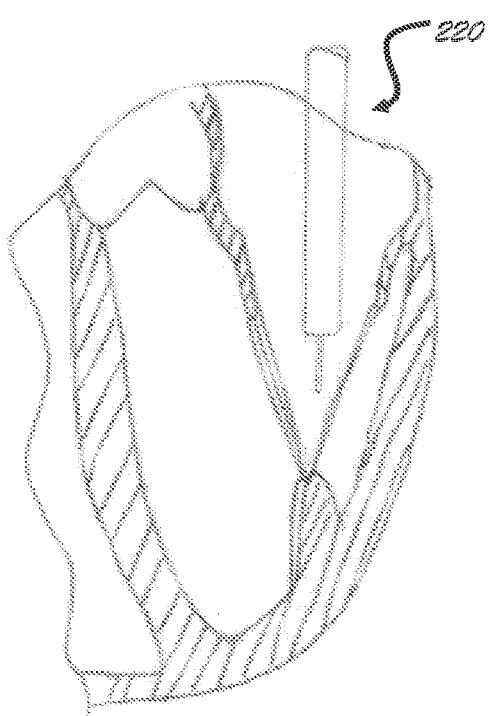
Figure 20:
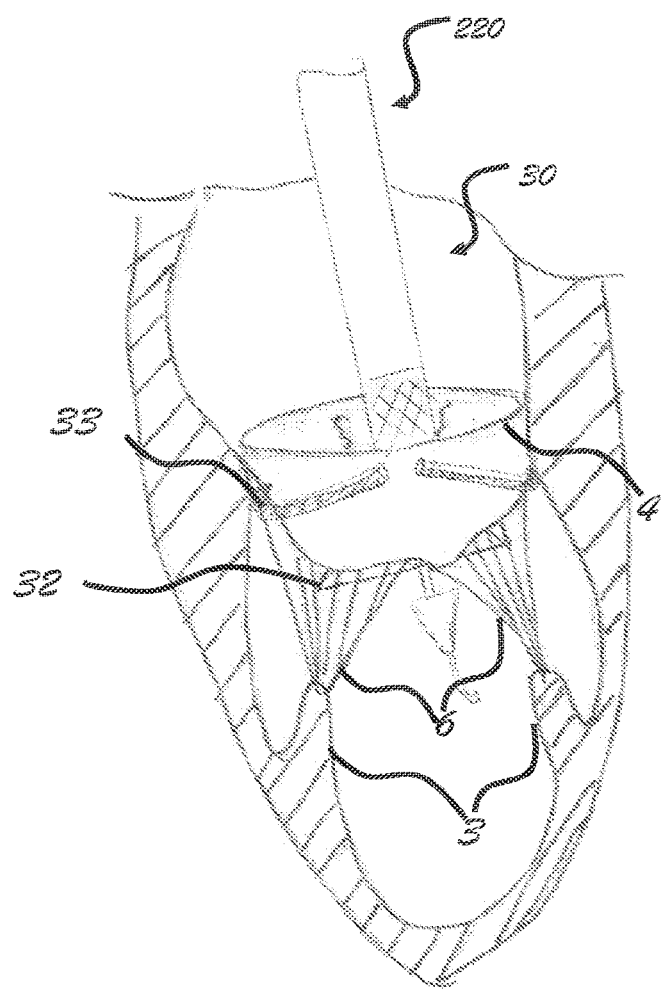
Figure 21:
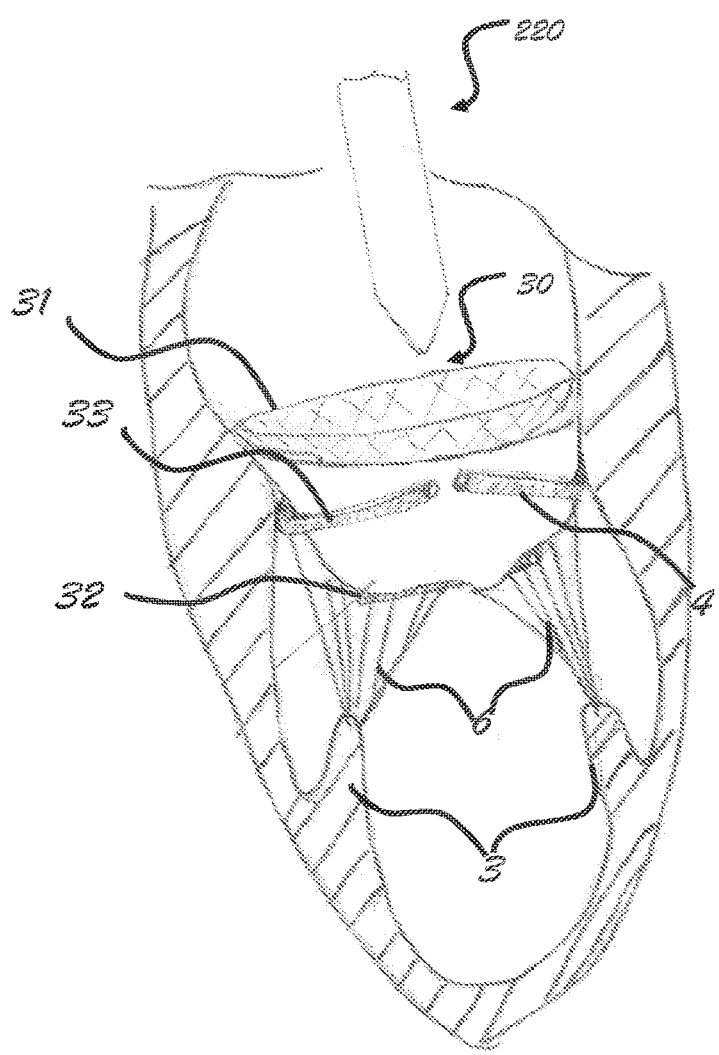

FIGS. 19A, 19B, 20, and 21 show an example of a trans atrial approach for trans catheter implantation in the mitral position. In FIGS. 19A and 19B, the catheter is advanced through the left atrium 8 and then through the native mitral valve to the left ventricle. The stent 30 in FIGS. 19A and 19B is crimped into the catheter shaft 220. The migration blocker rods are as well crimped in the shaft 220 and can be crimped distally toward the apex 16, proximally toward the entering point to the left atrium, or on top of the main frame 30. FIG. 20 shows the deployment of the stent 30. The migration blocker rods 33 pass through the chordae 6 under the native commissures and circle the native leaflets. The migration blocker rods 33 are configured, in certain embodiments, to bypass or encircle the native leaflets without clamping them to the main frame 30. Then, a completion of the deployment results in clamping the native annulus and allowing the rods 33 to prevent migration and rocking. FIG. 21 shows that the catheter 220 is withdrawn backwards after completion of the deployment.

Figure 22A:
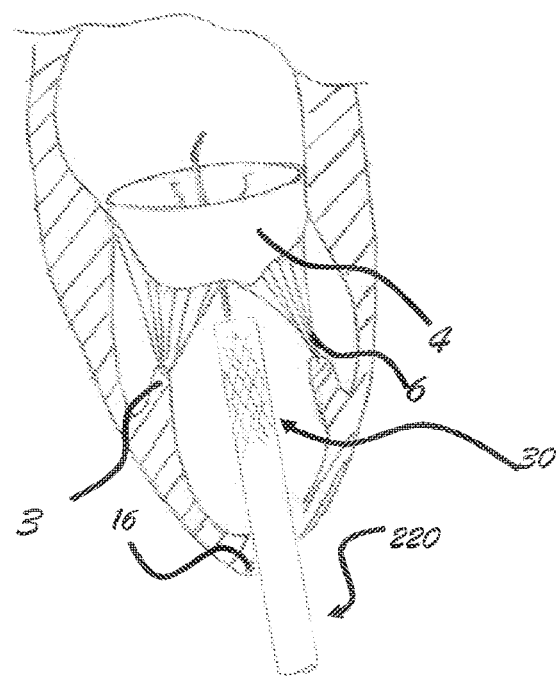
FIGS. 22A, 22B, 23, and 24 show an example of a trans apical approach for trans catheter implantation of a stent in the mitral position according to one embodiment.
Figure 22B:
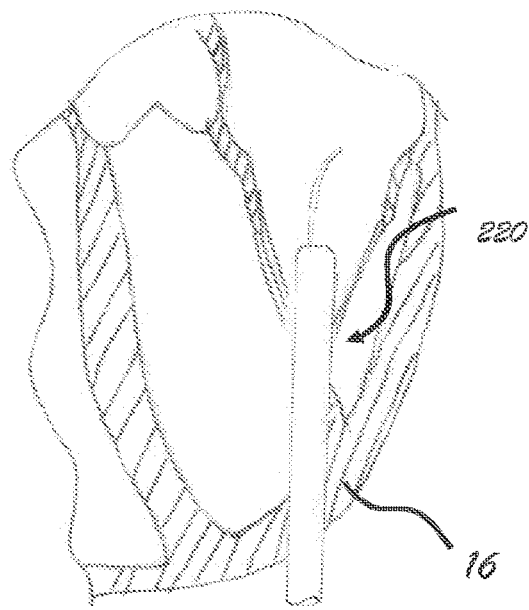
Figure 23:
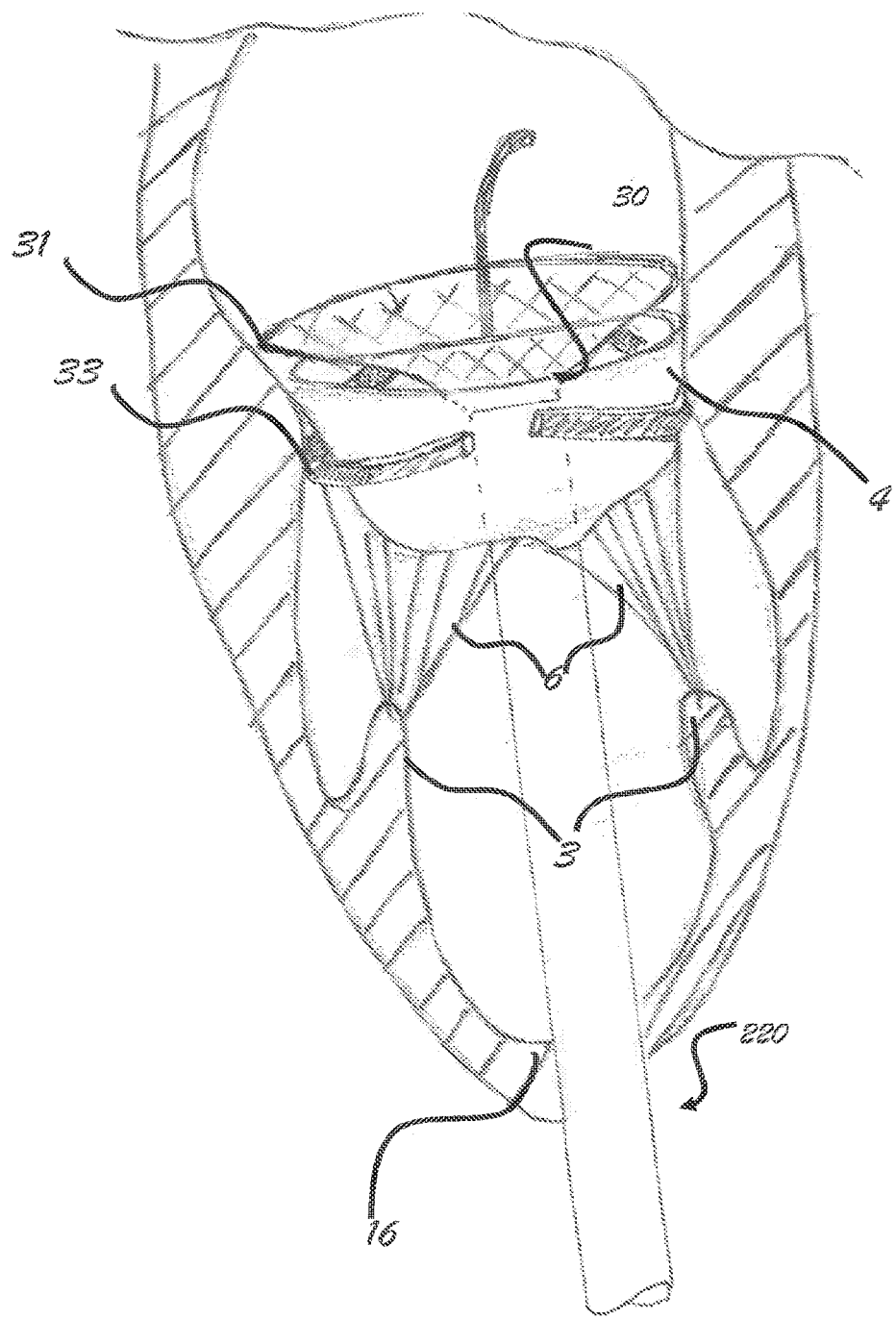
Figure 24:
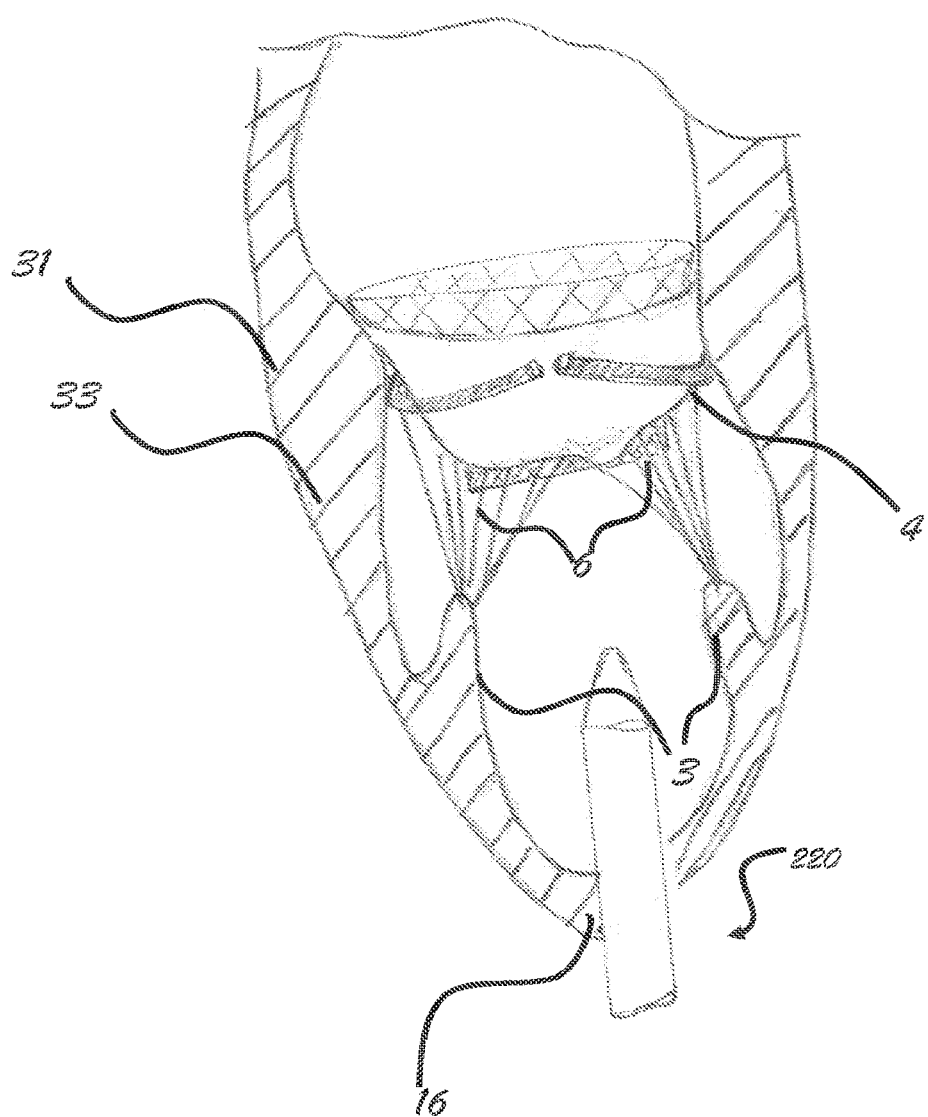

FIGS. 22A, 22B, 23, and 24 show an example of a trans apical approach for trans catheter implantation in the mitral position. In FIGS. 22A and 22B, the catheter shaft 220 is advanced through the apex 16 of the heart and then through the native mitral valve to the left atrium. The stent 30 in FIGS. 22A and 22B is crimped into the catheter shaft 220. The migration blocker rods are as well crimped in the shaft and can be crimped distally toward the atrium, proximally toward the entering point to the apex 16, or on top of the main frame 30. FIG. 23 shows the deployment of the stent 30. The migration blocker rods 33 pass through the chordae 6 under the native commissures and circle the native leaflets. Then, a completion of the deployment results in clamping the native annulus and allowing the rods 33 to prevent migration and rocking. FIG. 24 shows that the catheter is withdrawn backwards after completion of the deployment.

It will be understood by those having skill in the art that many changes may be made to the details of the above-described embodiments without departing from the underlying principles of the invention. The scope of the present invention should, therefore, be determined only by the following claims.

What is claimed is:

1. A prosthesis for securing a percutaneously implantable replacement valve in a heart, comprising:
   a radially expandable inflow section configured, in an expanded configuration of the prosthesis, to be implanted within an atrium of a heart adjacent a native valve annulus of a heart valve, the inflow section including a proximal opening and a distal opening, the proximal opening having a greater circumference than that of the distal opening such that the inflow section is tapered;
   a radially expandable outflow section coupled to the distal opening of the inflow section, the outflow section configured, in the expanded configuration, to be implanted through the native valve annulus and at least partially within a ventricle of the heart; and
   two or more migration blocker rods extending circumferentially around at least a portion of the outflow section, a gap between the two or more migration blockers and the outflow section configured to hold native leaflets of the heart valve;
   wherein, in a contracted configuration, the prosthesis is configured to be implanted through a catheter into the heart;
   wherein, in the expanded configuration, the tapered shape of the inflow section in the atrium cooperates with the two or more migration blockers in the ventricle to hold the prosthesis against the native valve annulus; and
   wherein respective ends of the two or more migration blocker rods are configured to lock together during implantation.

2. The prosthesis of claim 1, wherein, in the expanded configuration, the proximal opening of the inflow section, the distal opening of the inflow section, and a circumference of the outflow section are each substantially circular.

3. The prosthesis of claim 1, wherein, in the expanded configuration, the proximal opening of the inflow section is elliptical, and the distal opening of the inflow section and a circumference of the outflow section are each substantially circular.

4. The prosthesis of claim 1, wherein, in the expanded configuration, the proximal opening of the inflow section, the distal opening of the inflow section, and a circumference of the outflow section are each elliptical.

5. The prosthesis of claim 1, wherein, in the expanded configuration, the proximal opening of the inflow section is substantially circular, and the distal opening of the inflow section and a circumference of the outflow section are each elliptical.

6. The prosthesis of claim 1, wherein the inflow section comprises a shape memory material, and wherein the outflow section comprises one or more rows of expandable struts.

7. The prosthesis of claim 1, wherein the two or more migration blocker rods comprise barbs configured to extend, in the expanded configuration, through the native valve annulus and lock into the inflow section.

8. The prosthesis of claim 1, wherein the inflow section and the outflow section are separable from one another, the prosthesis further comprising a plurality of attachment members to removably couple the outflow section to the inflow section.

9. The prosthesis of claim 1, wherein the inflow section is configured to secure a replacement valve.

10. A prosthesis for securing a percutaneously implantable replacement valve in a heart, comprising:

a radially expandable inflow section configured, in an expanded configuration of the prosthesis, to be implanted within an atrium of a heart adjacent a native valve annulus of a heart valve, the inflow section including a proximal opening and a distal opening, the proximal opening having a greater circumference than that of the distal opening such that the inflow section is tapered;

a radially expandable outflow section coupled to the distal opening of the inflow section, the outflow section configured, in the expanded configuration, to be implanted through the native valve annulus and at least partially within a ventricle of the heart; and two or more migration blocker rods extending circumferentially around at least a portion of the outflow section, a gap between the two or more migration blockers and the outflow section configured to hold native leaflets of the heart valve;

wherein, in a contracted configuration, the prosthesis is configured to be implanted through a catheter into the heart;

wherein, in the expanded configuration, the tapered shape of the inflow section in the atrium cooperates with the two or more migration blockers in the ventricle to hold the prosthesis against the native valve annulus; and wherein the two or more migration blocker rods comprise barbs configured to extend, in the expanded configuration, through the native valve annulus and lock into the inflow section.

11. The prosthesis of claim 10, wherein, in the expanded configuration, the proximal opening of the inflow section, the distal opening of the inflow section, and a circumference of the outflow section are each substantially circular.

12. The prosthesis of claim 10, wherein, in the expanded configuration, the proximal opening of the inflow section is elliptical, and the distal opening of the inflow section and a circumference of the outflow section are each substantially circular.

13. The prosthesis of claim 10, wherein, in the expanded configuration, the proximal opening of the inflow section, the distal opening of the inflow section, and a circumference of the outflow section are each elliptical.

14. The prosthesis of claim 10, wherein, in the expanded configuration, the proximal opening of the inflow section is substantially circular, and the distal opening of the inflow section and a circumference of the outflow section are each elliptical.

15. The prosthesis of claim 10, wherein the inflow section comprises a shape memory material, and wherein the outflow section comprises one or more rows of expandable struts.

16. The prosthesis of claim 10, wherein the inflow section and the outflow section are separable from one another, the prosthesis further comprising a plurality of attachment members to removably couple the outflow section to the inflow section.

17. The prosthesis of claim 10, wherein the inflow section is configured to secure a replacement valve.

* * * * *